(12) United States Patent
Chiao et al.

(10) Patent No.: US 9,289,584 B2
(45) Date of Patent: Mar. 22, 2016

(54) REMOTELY CONTROLLED DRUG DELIVERY SYSTEMS

(75) Inventors: Mu Chiao, Richmond (CA); John K. Jackson, West Vancouver (CA); Fatemeh N. Pirmoradi, Vancouver (CA); Kevin Ou, Toronto (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 730 days.

(21) Appl. No.: 13/509,387

(22) PCT Filed: Sep. 13, 2011

(86) PCT No.: PCT/IB2011/002535
§ 371 (c)(1),
(2), (4) Date: May 11, 2012

(87) PCT Pub. No.: WO2012/035429
PCT Pub. Date: Mar. 22, 2012

(65) Prior Publication Data
US 2012/0226265 A1 Sep. 6, 2012

Related U.S. Application Data

(60) Provisional application No. 61/382,351, filed on Sep. 13, 2010.

(51) Int. Cl.
*A61M 31/00* (2006.01)
(52) U.S. Cl.
CPC .................................. *A61M 31/002* (2013.01)
(58) Field of Classification Search
CPC ...... A61K 38/00; A61M 31/002; C07K 14/47
See application file for complete search history.

(56) References Cited

U.S. PATENT DOCUMENTS

| | | |
|---|---|---|
| 3,527,220 A | 9/1970 | Summers |
| 5,830,207 A | 11/1998 | Leeb et al. |
| 6,077,299 A | 6/2000 | Adelberg et al. |
| 6,409,656 B1 | 6/2002 | Sangouard et al. |
| 6,537,256 B2 | 3/2003 | Santini, Jr. et al. |
| 6,551,838 B2 | 4/2003 | Santini, Jr. et al. |
| 6,689,380 B1 | 2/2004 | Marchitto et al. |
| 6,849,463 B2 | 2/2005 | Santini, Jr. et al. |
| 6,850,803 B1 | 2/2005 | Jimenez et al. |

(Continued)

FOREIGN PATENT DOCUMENTS

| | | |
|---|---|---|
| AR | 064985 A1 | 5/2009 |
| AU | 2002324312 A1 | 3/2003 |

(Continued)

OTHER PUBLICATIONS

Royal Society of Chemistry, "Magnets control drug release," accessed at http://www.rsc.org/Publishing/ChemTech/Volume/2009/05/magnets_drug_release.asp, posted on Mar. 30, 2009, 2 pages.

(Continued)

*Primary Examiner* — Imani Hayman
(74) *Attorney, Agent, or Firm* — Foley & Lardner LLP

(57) ABSTRACT

Drug delivery devices responsive to at least one external stimulus are described, along with methods for their preparation and use. The devices can be configured to respond to the stimulus, providing "on demand" release of one or more deliverables such as pharmaceutical drugs.

19 Claims, 11 Drawing Sheets

(56) References Cited

U.S. PATENT DOCUMENTS

| | | | |
|---|---|---|---|
| 6,976,982 | B2 | 12/2005 | Santini, Jr. et al. |
| 7,070,590 | B1 | 7/2006 | Santini, Jr. et al. |
| 7,582,080 | B2 | 9/2009 | Santini, Jr. et al. |
| 7,879,019 | B2 | 2/2011 | Santini, Jr. et al. |
| 7,879,027 | B2 | 2/2011 | Trieu |
| 7,942,867 | B2 | 5/2011 | Hood et al. |
| 2002/0099359 | A1* | 7/2002 | Santini et al. ............... 604/521 |
| 2002/0143284 | A1 | 10/2002 | Tu et al. |
| 2003/0036746 | A1 | 2/2003 | Penner et al. |
| 2004/0032187 | A1 | 2/2004 | Penner et al. |
| 2004/0121486 | A1 | 6/2004 | Uhland et al. |
| 2004/0229295 | A1 | 11/2004 | Marchitto et al. |
| 2004/0230182 | A1 | 11/2004 | Heruth et al. |
| 2004/0267234 | A1 | 12/2004 | Heart et al. |
| 2006/0178655 | A1 | 8/2006 | Santini, Jr. et al. |
| 2007/0147170 | A1 | 6/2007 | Hood et al. |
| 2007/0196281 | A1 | 8/2007 | Jin et al. |
| 2007/0276337 | A1 | 11/2007 | Trieu |
| 2008/0191581 | A9 | 8/2008 | Penner et al. |
| 2008/0208335 | A1 | 8/2008 | Blum et al. |
| 2008/0221557 | A1 | 9/2008 | Santini et al. |
| 2009/0162249 | A1 | 6/2009 | Hood et al. |
| 2009/0162250 | A1 | 6/2009 | Hood et al. |
| 2010/0094105 | A1 | 4/2010 | Porat et al. |
| 2011/0172587 | A1 | 7/2011 | Santini, Jr. et al. |
| 2011/0178578 | A1 | 7/2011 | Porat et al. |

FOREIGN PATENT DOCUMENTS

| | | |
|---|---|---|
| AU | 2008207990 A1 | 7/2008 |
| BR | PI0806820 A2 | 9/2011 |
| CA | 2675772 A1 | 7/2008 |
| CN | 101641631 A | 2/2010 |
| EP | 1626675 A2 | 2/2006 |
| EP | 2106566 A1 | 10/2009 |
| JP | 2007525237 A | 9/2007 |
| JP | 2010517081 A | 5/2010 |
| KR | 20090089916 A | 8/2009 |
| MX | 2009007743 A | 7/2009 |
| SU | 82150 A1 | 11/1949 |
| TW | 200848001 A | 12/2008 |
| WO | WO-81/00209 A1 | 2/1981 |
| WO | WO 03/015839 A2 | 2/2003 |
| WO | WO2004/093725 A2 | 11/2004 |
| WO | WO2007/056473 A2 | 5/2007 |
| WO | WO2008/030832 A1 | 3/2008 |
| WO | WO2008/091859 A1 | 7/2008 |

OTHER PUBLICATIONS

International Search Report and Written Opinion for PCT/IB2011/002535 dated Mar. 5, 2012.

Bock et al., Bevacizumab as a Potent Inhibitor of Inflammatory Corneal Angiogenesis and Lymphangiogenesis, *Invest Ophthalmol Vis Sci* (Jun. 2007), 48(6):2545-2552.

Bongaerts et al., Soft-tribology: Lubrication in a compliant PDMS-PDMS contact, *Tribology International* (Oct.-Dec. 2007), 40(10-12):1531-1542 (Abstract).

Cruz et al., Pharmacological approach to diabetic retinopathy, *Diabetes Metab Res Rev* (Mar.-Apr. 2004), 20(2):91-113 (Abstract).

Gong, Friction and lubrication of hydrogels—its richness and complexity, *Soft Matter* (Mar. 2, 2006), 2:544-552 (Abstract).

Intra et al., Pulsatile release of biomolecules from polydimethylsiloxane (PDMS) chips with hydrolytically degradable seals, *Journal of Controlled Release* (Dec. 6, 2007), 127:280-287.

Jackson et al., The inhibition of angiogenesis by antisense oligonucleotides to clusterin, *Angiogenesis* (Jun. 9, 2005), 8(3):229-238 (Abstract).

Myles et al., Recent progress in ocular drug delivery for posterior segment disease: Emphasis on transscleral iontophoresis, *Advanced Drug Delivery Reviews* (Dec. 13, 2005), 57(14):2063-2079 (Abstract).

Ou et al., A Passive Check Valve Using Microspheres for Low Pressure and Low Flow Rate Applications, *Transducers' 11*, Beijing, China (Jun. 5-9, 2011), pp. 1785-1788.

Ou et al., Presentation: A Passive Check Valve Using Microspheres for Low Pressure and Low Flow Rate Applications, *Transducers'11*, Beijing, China (Jun. 5-9, 2011) [printed from internet Apr. 4, 2012].

Owen et al., A PLGA membrane controlling cell behavior for promoting tissue regeneration, *Biomaterials* (Dec. 2005), 26(35):7447-7456 (Abstract).

Pirmoradi, Presentation: A Battery-less MEMS Device for On-demand and Controlled Drug Delivery, May 25, 2011, Department of Mechanical Engineering, University of British Columbia, Canada.

Pirmoradi et al., Magnetic poly(dimethyelsiloxane) composite membrane incorporated with uniformly dispersed, coated iron oxide nanoparticles, *J Micromech Microeng* (Oct. 23, 2009), 20:1-7.

Pirmoradi et al., A magnetically controlled MEMS device for drug delivery: design, fabrication, and testing, *Lab Chip* (May 22, 2011), 11:3072-3080.

Pirmoradi et al., On-demand controlled release of docetaxel from a battery-less MEMS drug delivery device, *Lab Chip* (Feb. 16, 2011), 11:2744-2752.

Pirmoradi et al., Delivery of an Anti-Cancer Drug From a Magnetically Controlled MEMS Device Show Cytotoxicity in PC3 and Huvec Cells, *Transducers'11*, Beijing, China (Jun. 5-9, 2011), pp. 2831-2834.

Unger et al., Monolithic Microfabricated Valves and Pumps by Multilayer Soft Lithography, *Science* (Apr. 7, 2000), 288:113-116.

Data & Statistics, http://www.visionhealth.ca/data/htm [printed from internet Apr. 5, 2012).

Speicher et al., Pharmacologic therapy for diabetic retinopathy, Expert Opinion on Emerging Drugs, (2003), vol. 8, Issue 1, pp. 239-250.

\* cited by examiner

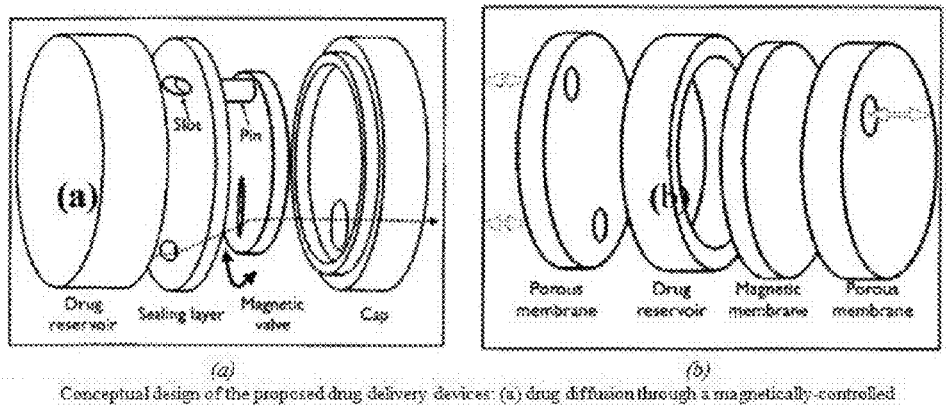

(a) Conceptual design of the proposed drug delivery devices: (a) drug diffusion through a magnetically-controlled rotating valve; (b) drug delivery using a magnetic membrane pump. Two holes on the porous membrane are shown to represent pores.

Fig. 1

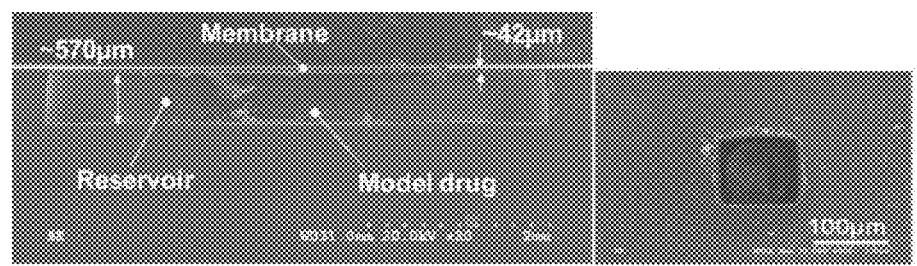

(a) Cross-section of a fabricated device showing free-standing magnetic membrane with residues of a model drug inside the reservoir; (b) Laser-drilled apertures in the magnetic membranes ablated using UV laser with 355 nm wavelength.

Fig. 2

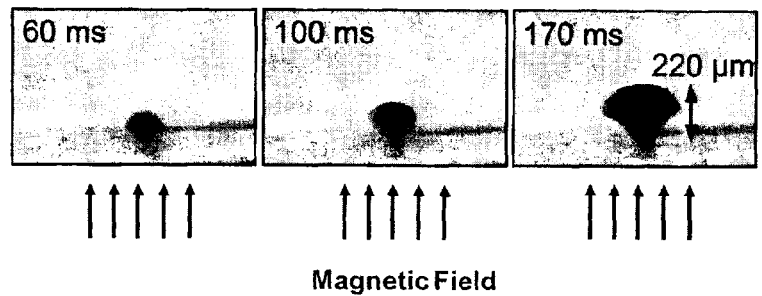
Fig. 3 Sequence of TB solution discharge under ~176 mT magnetic field
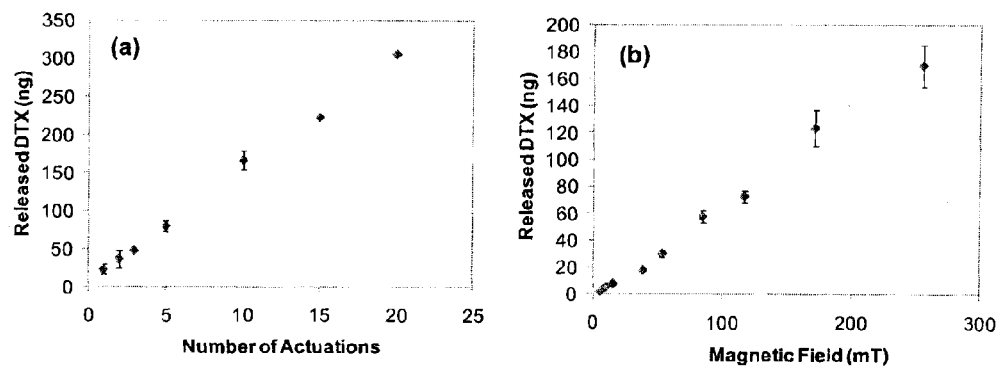
Fig. 4 (a) Amount of released DTX from a device operated with various numbers of actuation cycles under 255 mT magnetic field. (b) Amount of released DTX in various magnetic fields when each data point corresponds to 10 actuation *cycles* for all points.

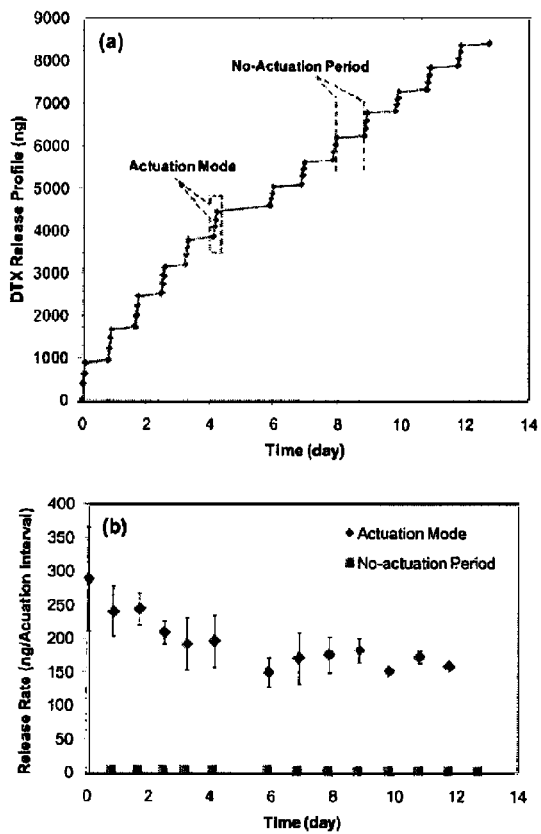

Fig. 5 Release profile of tritium-labeled DTX from a device (membrane: ⌀6 mm × t=40 μm, aperture: 100 × 100 μm², reservoir depth: ~500 μm) operated under 255 mT magnetic field (a) Cumulative DTX release includes a series of *actuation modes* followed by *no-actuation periods*. Each data point represents ten consecutive *actuation cycles*, (b) Average DTX release rates of the device. Diamonds represent the average of the release rates for three consecutive *actuation intervals*. Squares represent the release rate in the *no-actuation* periods.

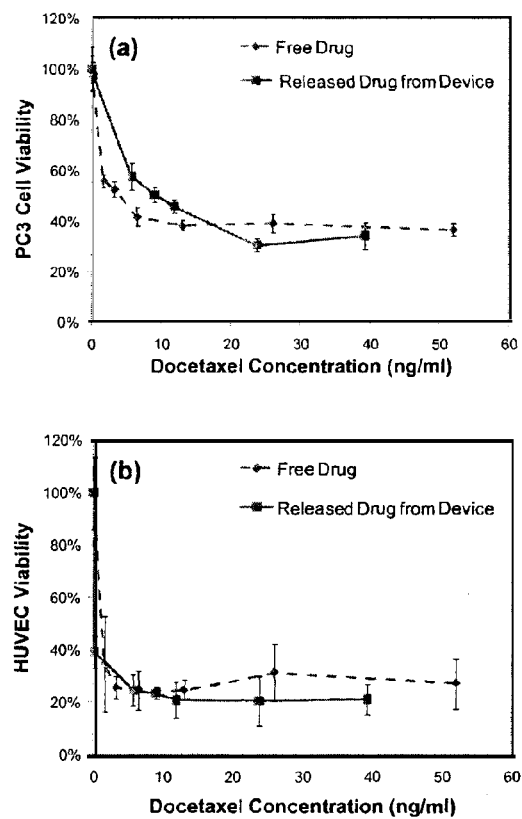
Fig. 6 (a) PC3 cells viability and (b) HUVECs viability following exposure to DTX both in the form of fresh free drug and DTX released from a device in various concentrations. The device was actuated under 255 mT magnetic (6 repeats for each condition).

The porous structure in the PDMS membrane after leaching of the diblock copolymer.

Cross-section of a porous PDMS membrane: after leaching PEG and salt particles, porous PDMS structure was left behind.

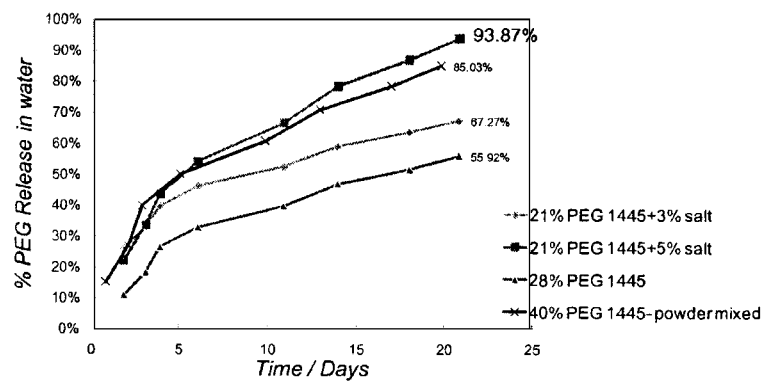
Fig. 9 Amount of PEG release after leaching the films in DI water at 80°C.

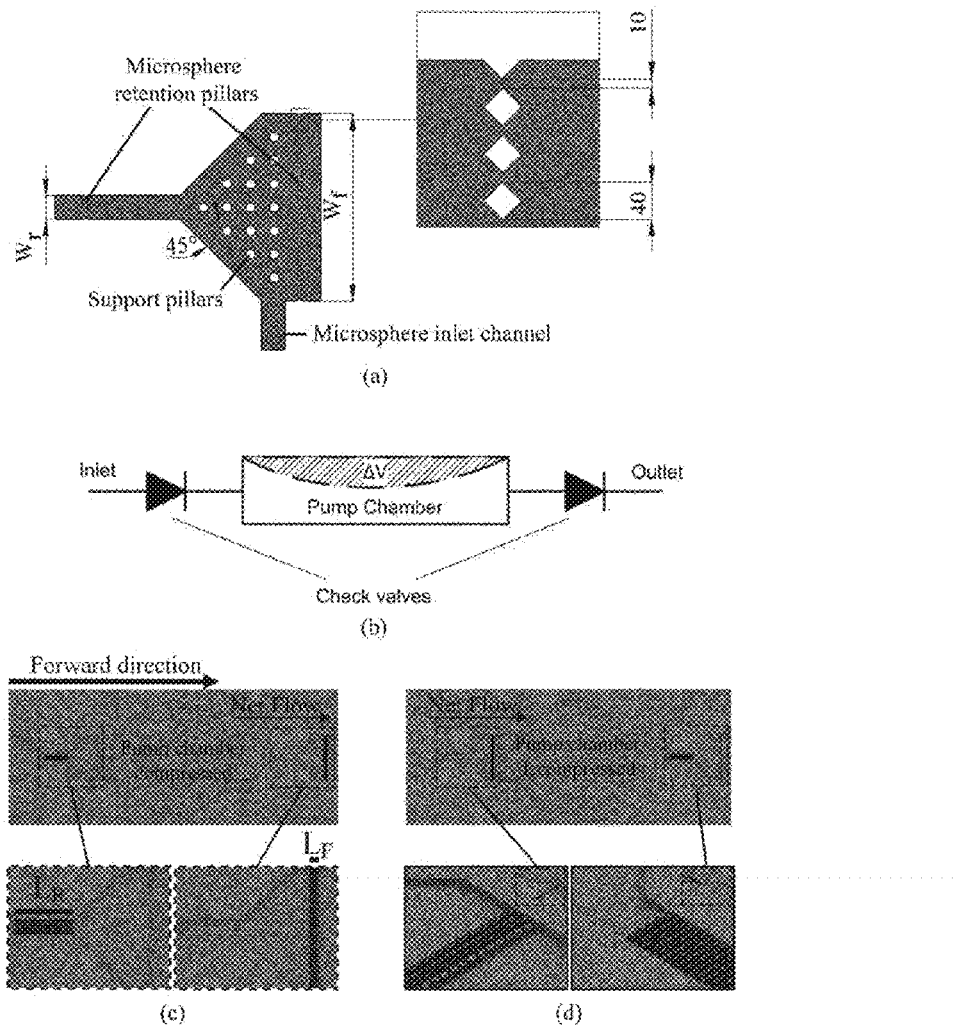

(a) Design of valve with reverse channel designated WR and forward channel designated WF; (b) Schematic of a pump with check valves at the inlet and outlet side of the reciprocating pump chamber; (c) Top view of the check valve with pump chamber showing microsphere position in inlet and outlet side of the valve chambers as the pump diaphragm compresses. Microspheres collect in reverse flow direction for the inlet side valve and collect in the forward flow direction for the outlet side valve; (d) Isometric view of pillars and microspheres in check valve when the pump chamber decompresses

Fig. 10

(a) Soft lithography technique used in fabricating check valve and micropump. (b) PDMS layers used to fabricate micropump in characterization experiments. (c) PDMS layers of manually actuated micropump used in trial drug diffusion study.

(a)                          (b)

(a) Microspheres collecting in reverse flow direction, (b) microspheres collecting in forward flow direction.

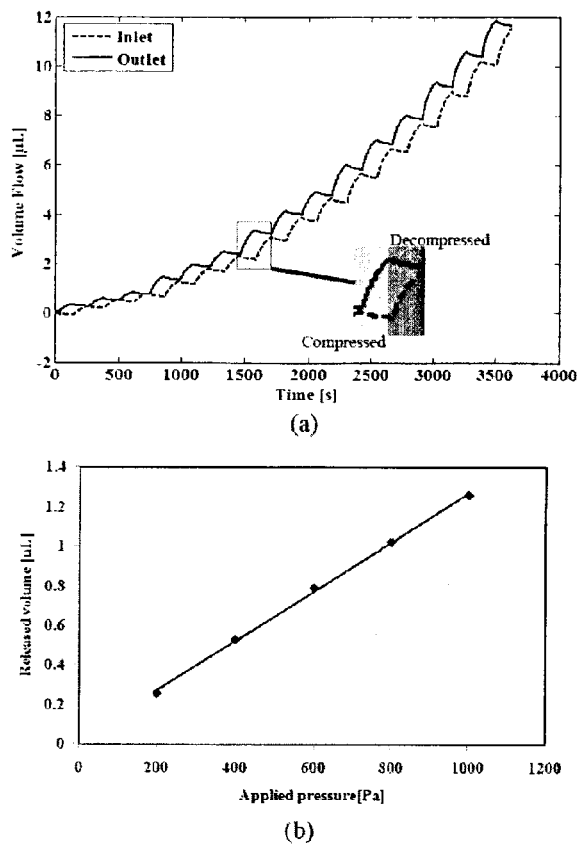
Fig 13: (a) Volume flow measurement of the micropump with 240 s cycle time and 50% duty cycle. Shaded areas show the volume flow of the micropump at inlet and outlet during one actuation cycle. (b) The average volume flow from the device versus applied pressure on the diaphragm

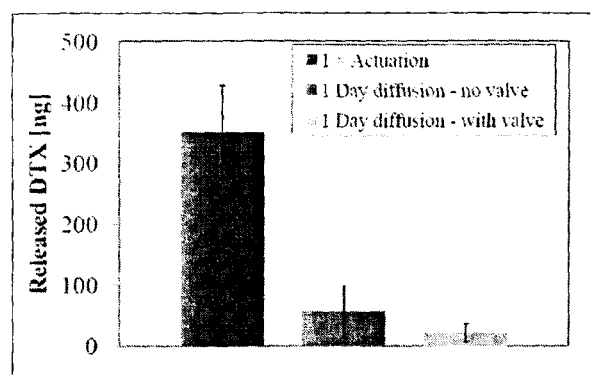
Fig. 14 DTX released through actuation and diffusion from devices with valves and without valves

REMOTELY CONTROLLED DRUG DELIVERY SYSTEMS

CROSS REFERENCE TO RELATED APPLICATION

This application is a U.S. national stage filing under 35 U.S.C. §371 of International Application No. PCT/IB2011/002535 filed on Sep. 13, 2011 entitled "Remotely Controlled Drug Delivery Systems," which claims benefit of priority to U.S. Provisional Application No. 61/382,351, filed on Sep. 13, 2010, the disclosure of which is hereby incorporated by reference in its entirety.

CLAIM OF PRIORITY

This application is a U.S. national stage filing under 35 U.S.C. §371 of International Application No. PCT/IB2011/002535 filed Sep. 13, 2011 entitled "Remotely Controlled Drug Delivery Systems," the disclosure of which is incorporated by reference in its entirety.

BACKGROUND

Drugs are usually delivered systemically by several methods including oral (tablets), parenteral (intravenous or intraperitoneally), topical (patches), pump (e.g. insulin pumps) administration. However, these methods expose the whole body to similar concentrations of the drug even though, usually, only a specific region of the body may require the drug. Also, the drug is usually cleared quite quickly from the body by the liver or kidneys so that, in order to maintain therapeutic concentrations of the drug, repeated drug administration is required. Furthermore, many areas of the body (such as bone or the disorganized growing regions of tumors) are poorly accessible to systemically administered drug so that high concentrations of the drug must be administered to reach therapeutic levels in the diseased tissue, resulting in especially high concentrations of the drug in all other non-diseased tissues. In summary, for many drugs systemic administration may be unnecessarily expensive and efficacy may be limited by dose limiting systemic drug toxicities and/or other factors.

Ideally, a drug should be delivered to the diseased site at a concentration that is optimal to treat the disease and be maintained at that concentration for the optimally required time. For example, diabetes is a systemic disease treated with insulin so that in some instances a pump system connected to an onboard blood glucose monitor that injects exactly the right amount of insulin to maintain optimal blood glucose levels might be considered an optimal drug delivery system.

Some drugs may be administered using implantable controlled release systems. For example, an injectable polymeric drug release system may be injected directly into a tumor and release the drug locally to kill cancer cells but the amount of drug released into the bloodstream may be insignificant so that systemic toxicity may be negligible. There are numerous examples in the literature describing injectable polymeric pastes or microspheres, for example, containing the anticancer drug paclitaxel. A gliadel™ wafer made from a polyanhydride containing an anticancer drug is approved for placement in brain tumor resection sites to kill residual cells. Stents, coated with paclitaxel in a polymer, may be placed in blood vessels to deliver the drug to the smooth muscle cells of the blood vessel to prevent proliferation and vessel closure.

With the exception of pumps, nearly all existing controlled release systems do not actually allow fine control of drug release. Usually the release profile is characterized by a burst phase of release followed by a continuous release at a slower rate. All rates may depend on geometry, injection conditions and/or other factors.

Improved controlled release systems would allow control of dose or timing of release and preferably both. This would allow external control of release as in an "on demand" system. Alternatively, an implanted system might be designed for a preprogrammed drug release without subsequent external control. This system might include, for example, a reservoir of drug implanted at a disease site with a built-in release system that provided drug at a schedule to fit a doctor's plan. These systems might also be used for radiotherapeutics whereby a sealed source was exposed to deliver a dose. Intra J et al, *Journal of controlled release*, 2008, 127, p 280-287 describe a system whereby a drug reservoir is covered with a PLGA membrane which degrades over time so that the drug may be released when the membrane degrades. The paper describes PLGA membranes with different degradation rates. This system acts as delayed release system where the delay may be controlled to some degree and therefore some scheduling of dosing may be achieved. The system does not allow for "on demand" drug release.

There has been much research completed in the area of microelectronic mechanical systems (MEMS) with drug release in mind. J. T. Santini, et al., "Microfabricated devices for the storage and selective exposure of chemicals and devices", U.S. Pat. No. 6,849,463, described the possibility of microchips with drug reservoirs that have electronic release systems. Although many aspects of such devices have been described the biggest hurdle remains the power supply. Battery systems are not yet small enough to allow for on board power sources on microchips. This power is provided via connections to external sources. Such systems obviously limit the viability of the device. For example a device fitted in the ocular or be to release drug to the retina would require wires to be exposed outside the body. This is undesirable for many reasons. In certain disease settings (e.g. where a heart pacemaker has already been installed with an on board power supply) an auxiliary drug release system might take power form such a device. Such arrangements, however, at least in theory decrease the time required between battery changes, and therefore expose the patient to more frequent surgeries.

An external electromagnetic source has been used to generate electrical current in an implantable metallic coil. The current is then stored in a capacitor. Power is drawn from the capacitor when needed. The sizes of the coil, the capacitor and controlling circuitry dominate the overall drug delivery device volume. As with battery-powered devices, size and space become issues and potential barriers to use.

An improved strategy would allow for an external stimulus or stimuli to effect the drug release. Such stimuli might involve focused sources such as, for example, radioactive radiation, electromagnetic radiation (e.g. radio waves or microwaves) or heat whereby a cover over a reservoir was disturbed by the stimuli to expose the contents of the reservoir. Some systems have been described that attempt to use these methods. Other systems have described polymer matrices containing magnetic particles and drugs so that on the application of a magnetic field the movement of the particles may enhance drug release rates. However, such a system allows background drug release with acceleration of release upon magnetic stimulation so that the ability to control dose is very limited. Details of these previously described systems are included in the references below: A heat source is used to release drug from a reservoir in US20040121486A1. Magnetism is used to vibrate particles in a drug loaded polymer in US20070196281A1. Ultrasound is used to release drug from a reservoir in US2004032187A1. A catheter and pump system is described in US20040230182A1. MEMS based drug delivery systems have been described (U.S. Pat. Nos. 7,070,590, 6,551,838 and 6,537,256). Membranes sealing drug-containing reservoirs can be broken by heat or electrochemical degradation, however, the process needs a battery and heat from the device may damage the drug. Some include RF charging of a magnetic coil with a magnetic shield for better RF coupling (U.S. Pat. No. 6,850,803) and electromagnetically triggered porosity changes in polymers to release drugs (U.S. Pat. No. 5,830,207). Another patent (U.S. Pat. No. 6,689,380) focuses on providing electromagnetic fields to charge an RF coil and circuitry on a drug delivery device. However none of these patents are related to direct electromagnetic-to-mechanical energy translation for MEMS drug delivery devices.

SUMMARY

Some embodiments provide a drug delivery device comprising a reservoir adapted to contain at least one deliverable; a release mechanism sealingly engaged with the reservoir to selectively release the at least one deliverable upon application of an external stimulus. In some embodiments, the release mechanism comprises a diaphragm membrane, a fracturable membrane, or a valve membrane.

Some embodiments provide a drug delivery device comprising a reservoir and the diaphragm membrane release mechanism. The diaphragm membrane comprises a polymeric matrix which is substantially non-porous to the at least one deliverable in a first state, and substantially porous to the at least one deliverable in a second state achieved in response to the external stimulus. In some embodiments, the porous membrane is composed of electrospun nanofibres containing or encapsulating magnetic particles or more than one electrospun membrane "sandwiches" magnetic particles.

In some such embodiments, the polymeric matrix comprises a plurality of suspended magnetic particles, which upon application of a magnetic field causes displacement of the diaphragm to the second state. The plurality of suspended magnetic particles may be coated ferromagnetic particles. In some embodiments, the coating comprises one or more hydrophobic surfactant. In some embodiments, the hydrophobic surfactant is selected from In some embodiments, the diaphragm is a polymeric matrix defining one or more pores wherein upon physical manipulation the one or more pores move from a substantially closed first state into a substantially open second state, due to displacement of the diaphragm.

In some embodiments, the release mechanism further comprises a material sensitive to electromagnetic radiation, such that upon exposure to electromagnetic radiation, the material fractures, breaking the sealing arrangement of the release mechanism to release the at least one deliverable. In some such embodiments, the material sensitive to electromagnetic radiation comprises gold nanoparticles. The external stimulus may be electromagnetic radiation in the form of a light source, such as a laser.

In some embodiments, the release mechanism is a valve membrane, comprising a non-movable layer defining at least one hole or pore at a pre-specified location on the non-movable layer, wherein the non-movable layer is sealingly engaged with the reservoir; a rotatable membrane defining at least one hole or pore which is rotatably affixed to the non-movable layer, such that the non-movable layer is positioned between the reservoir and the rotatable membrane; when the rotatable membrane is moved at least one hole or pore of each of the non-movable layer and the rotatable membrane are aligned allowing release of the deliverable.

In some embodiments, the membrane, either in the valve configuration or the diaphragm configuration may comprise a valve to regulate the amount drug delivery in each pumping cycle. In some embodiments, the valve is selected from a check valve or a flow-limiting valve. In some embodiments, this valve is made up of one or more microchannels containing one or more microspheres which act to either allow or stop the flow within the microchannel(s).

In some embodiments, the drug delivery device contains a deliverable stored within the reservoir. The deliverable, in some embodiments, comprises one or more active pharmaceutical ingredients. The active pharmaceutical ingredient can be selected from an antiangiogenic drug, an antiproliferative, an anti-inflammatory, an anticancer drug, an antiglaucoma, antiretinopathy drug, a drug that improves orthopedic outcome, and combinations thereof.

In some embodiments, the device is sized and configured for implantation in one or more of under the eyelid, behind the eye, or intraocularly to treat ocular disorders. The device may comprise a contact lens shaped device to release one or more drugs from the lens to the surface of the eye. In other embodiments, the device is sized and configured for implantation at or near a patient's body to be treated where the part of the body or disease to be treated is a pelvic fracture, bone fracture, urological, bone, cancer, arthritis, infections, ocular, neurological, endocrinological, vascular or inflammatory. For example, a device as described herein may be placed at or near a fracture site to deliver anti-inflammatories, or compounds that facilitate bone mending.

Some embodiments provide a device comprising a polymeric membrane which changes shape in response to an external stimuli to cause a change in focal length of a contact lens to correct for vision problems.

Some embodiments provide a method of using such devices to treat various diseases, disorders, or conditions. Such methods provide for local release of a deliverable, the method comprising positioning any of the above-described drug delivery device at a site in need of receiving the deliverable; and applying an external stimulus at or near the drug delivery device to release the deliverable.

Some embodiments provide a kit comprising a drug delivery device and an external stimulus generating source. In some such kits, the external stimulus generating source is a magnetic field generator, such as a magnet.

BRIEF DESCRIPTION OF DRAWINGS

FIG. 1 shows a conceptual design of several drug delivery devices. FIG. 1($a$) shows drug diffusion through a magnetically-controlled rotating valve. From left to right, the components are a drug reservoir, a sealing layer with a slot, a magnetic valve with a pin, and a cap. FIG. 1($b$) shows drug delivery using a magnetic membrane pump. Two holes on the porous membrane are shown to represent pores. From left to right, the components are a porous membrane with two pores, a drug reservoir, a magnetic membrane, and a porous membrane.

FIG. 2($a$) shows a cross-section of a fabricated device showing free-standing magnetic membrane with residues of a model drug inside the reservoir. FIG. 2($b$) shows laser-drilled apertures in the magnetic membranes ablated using UV laser with 355 nm wavelength.

FIG. 3 shows a time sequence of TB solution discharge under approximately 176 mT magnetic field.

FIG. 4(a) shows the amount of released DTX from a device operated with various numbers of actuation cycles under 255 mT magnetic field. FIG. 4(b) shows the amount of released DTX in various magnetic fields when each data point corresponds to 10 actuation cycles for all points.

FIG. 5 shows the release profile of tritium-labeled DTX from a device (membrane:Ø6 mm×t=40 μm, aperture: 100× 100 μm², reservoir depth: approximately 500 μm) operated under 255 mT magnetic field. FIG. 5(a) shows cumulative DTX release includes a series of actuation modes followed by no-actuation periods. Each data point represents ten consecutive actuation cycles. FIG. 5(b) shows average DTX release rates of the device. Diamonds represent the average of the release rates for three consecutive actuation intervals. Squares represent the release rate in the no-actuation periods.

FIG. 6(a) shows PC3 cells viability, and FIG. 6(b) shows HUVECs viability, both following exposure to DTX both in the form of fresh free drug and DTX released from a device in various concentrations. The device was actuated under 255 mT magnetic (6 repeats for each condition).

FIG. 9 shows the amount of PEG release after leaching the films in DI water at 80° C.

FIG. 10(a) shows a design of valve with reverse channel designated WR and forward channel designated WF. FIG. 10(b) is a schematic of a pump with check valves at the inlet and outlet side of the reciprocating pump chamber. FIG. 10(c) is a top view of the check valve with pump chamber showing microsphere position in inlet and outlet side of the valve chambers as the pump diaphragm compresses. Microspheres collect in reverse flow direction for the inlet side valve and collect in the forward flow direction for the outlet side valve. FIG. 10(d) is an isometric view of pillars and microspheres in check valve when the pump chamber decompresses.

FIG. 13(a) shows volume flow measurement of the micro pump with 240 second cycle time and 50% duty cycle. Shaded areas show the volume flow of the micro pump at inlet and outlet during one actuation cycle. FIG. 13(b) shows the average volume flow from the device versus applied pressure on the diaphragm.

FIG. 14 shows DTX released through actuation and diffusion from devices with valves and without valves.

DETAILED DESCRIPTION

Abbreviations and Definitions

Figure 7:
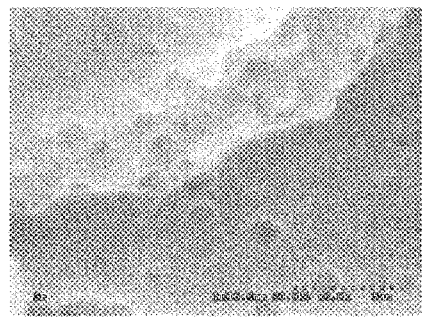
FIG. 7 shows the porous structure in the PDMS membrane after leaching of the diblock copolymer.

This application relates to the area of delivery of therapeutic agents to the body. The method involves placing a device comprising a reservoir of drug and a release mechanism that is controlled by an external stimulus, such as a physical manipulation, a magnetic field, or a light source, at or near a body part or area in need of treatment.

Abbreviations:
PDMS: polydimethylsiloxane, PLGA: poly lactic co glycolic acid, PMMA: Poly methyl methacrylate, PCL: Polycaprolactone, EVA: Poly ethylenevinyl acetate.

Definitions:
The term "Toxic" as used herein refers to a condition where a human or animal responds negatively or poorly to exposure to a material.

The term "Biocompatible" as used herein refers to a material that is well tolerated by a human or animal upon implantation of the material in the body.

The term "Reservoir" as used herein refers to materials that may hold solids or liquids, and define an open area that may be covered. The term may also refer to a material that holds a drug and the material/drug complex is covered.

The term "Treatment" as used herein refers to alleviation of symptoms associated with a disease state or patient morbidity. The term does not necessarily mean providing a cure but may include disease prevention, inhibiting disease progression or facilitating recovery.

The term "Drug" as used herein refers to a therapeutic agent. These agents may include proteins, peptides, nucleic acids, isotopes, chemical or other molecule that provides treatment.

The term "deliverable" as used herein refers to any agent that is desired to be released locally. Deliverables include, but are not limited to active medical substances, pharmacological ingredients, pharmaceuticals, drugs, antibodies, vitamins, nutritional products, etc. and may be liquids, solids, gels, etc.

The term "magnetic" as used herein refers to the property of being affected by a magnetic field, the term therefore refers to actual magnets, and to materials that are not themselves magnets, but are affected by a magnetic field. For example, iron oxide particles, although not necessarily magnets themselves, are "magnetic" because they are drawn to a magnetic field, a magnet is "magnetic" because it may be repulsed or attracted by another magnet.

The term "pore" as used herein refers to an aperture in a membrane which may comprise a hole or many holes or may simply refer to a more porous state than surrounding materials.

The term "medical substance" as used herein refers to any agent that produces an improvement in the health of a human or animal and may include drugs.

The term "surface modified" refers to surfaces that have been modified by the addition of molecules that hide the original surface.

Methods and apparatus are described herein that allow for "on demand" controlled drug release using external stimuli. Generally the apparatus relate to small implantable devices with reservoirs for containing and delivering one or more agent drugs with membrane coverings over the reservoir to prevent drug release until desired. The description herein focuses on devices suitable for implantation with the patient's body. In some instances, however, the device is surface mountable, as in the case for some corneal or topical applications.

Upon application of an external stimulus or stimuli, the seal between the device and the covering may be compromised allowing aqueous fluids (blood, interstitial fluid etc.) to enter the reservoir and release the drug either via mixing and release or simply via a more direct release approach, or combination thereof.

Alternatively, the covering may be partially porous and elastic so that upon stimulation the membrane moves causing pressure difference between the inside and the outside of the reservoir so that water can enter, dissolve drug and "squeeze"

the drug solution out of the reservoir through the porous covering. An actual pore or hole could be incorporated into the membrane to allow drug efflux.

In another embodiment, the reservoir might have inlet/outlet apertures with or without valves so that the magnetic membrane does not contain pores but drug is released through the apertures.

In another embodiment, a brittle polymer film may be stimulated so that vibrations crack the film and drug may be released from a reservoir. In another embodiment, the membrane may be elastic and the reservoir may contain a puncture device (e.g. a pin at the base of the reservoir) so that as the elastic membrane vibrates over the puncture device the membrane may puncture and the drug may be released. Alternatively, the sealing membrane may have a hole and can be sliding against the drug reservoir underneath, drug can released when proper alignment occurs between the hole and the drug reservoir.

Exemplary designs of the proposed drug delivery devices are shown in FIG. 1. FIG. 1(a) depicts an exemplary device, described in further detail below, suitable for drug diffusion through a magnetically-controlled rotating valve. FIG. 1(b) depicts an exemplary device, described further below suitable for drug delivery using a magnetic membrane pump. Two holes on the porous membrane represent pores. As discussed herein, various embodiments may employ as few as one pore or a plurality of pores to facilitate release.

In some embodiments, the apparatus described comprises a polymer membrane containing magnetic particles, whereby the membrane acts as a seal over the reservoir. The device may be implanted at or near the body part or area that would benefit from treatment. In some instances, the implantation is below the skin. Upon application of an external magnetic field at a point near the implanted device, the membrane may deform in response. The external magnetic field could also or alternatively be applied without direct contact, depending on the strength of the magnet. Alternatively the magnet may be introduced through a body cavity (e.g. anus, vagina, oral or nasal) to activate a device close to that area. This deformation of the membrane is used to trigger the breakage of a seal, breakage of the membrane, pumping of water through a porous membrane, opening of one or more pore, or puncture of a membrane.

In another aspect, the magnetic particles may coat the rim of the reservoir and be covered by a membrane. Upon stimulation of the magnetic particles by an external magnetic field, the particles may vibrate and compromise the seal between the membrane and the reservoir to release the drug.

In some aspects the drug delivery device will comprise a thin reservoir section made from a polymer, e.g. PDMS, filled with a deliverable, e.g. an antiangiogenic drug, overlaid with a thin magnetic membrane which contains a single or multiple laser cut holes. The magnetic membrane can be further covered with a protective thin perforated rigid polymer membrane (e.g. made from PCL, or a PLGA-PEG composite) that may prevent tissue deformation of the magnetic membrane. This device may be surgically implanted by a simple procedure near the treatment site, e.g. behind the eye.

In another aspect, the magnetic particles may be replaced or augmented by the inclusion of gold nanoparticles. Upon application of an external laser light source these gold nanoparticles undergo plasmon resonance and begin to heat. The heat may then compromise the seal between the membrane and a drug filled reservoir. The wavelength of light that must be used to achieve plasmon resonance is dependent on many factors such as the size of the particles. Generally speaking, large (e.g., 230 nm) gold nanoparticles heat in the NIR range whereas smaller (e.g., 30 nm) do not (30 nm nanoparticles heat at 530 nm), but it is possible to specially adapt the gold particles to make them resonate in the near infra red. Although visible light may penetrate tissue to some degree, NIR may penetrate 8-10 cm from a source at the skin allowing access to most tissue regions. Alternatively a simple thin injection feed optic fiber system may allow access to the local environment of an implanted device so that any wavelength of light might be used.

In one aspect this system is a drug loaded reservoir covered by a polymer membrane. Using encapsulation and manufacturing techniques described herein, a polymer film containing magnetic particles that are distributed homogenously through the film can be prepared. Upon implantation in an aqueous environment, the drug remains trapped in the reservoir with some minor leakage of drug being acceptable. Upon application of an external stimulus, the membrane may deflect, crack, or otherwise change to trigger a release mechanism that allows controlled doses of drug to be released.

In another aspect, the magnet actuates a magnetic valve that allows drug to release.

The devices disclosed herein may be used to deliver numerous types of drugs to numerous disease sites. A device of this type may deliver anticancer drugs to tumor or tumor resection sites or may deliver antiarthritic or orthopaedic drugs to musculoskeletal sites. The device may deliver drugs to eyes to treat such diseases as glaucoma, retinopathy or macular degeneration.

In some embodiments, drugs for various treatments include more hydrophobic drugs since highly water soluble drugs may fully dissolve in an aqueous-filled reservoir resulting in rapid release of contents or possible drug degradation over time. This may not always be the case, where for example the drugs are water stable and the actuation method allows the release of a small fraction of the drug contents.

In some aspects, the drug can be an antiangiogenic drug such as docetaxel, paclitaxel, camptothecin, doxorubicin, 1,4 naphthoquinones, etoposide, or antibodies, apatmers, isotopes, or prostaglandin analogues and other glaucoma, retinopathy and macular degeneration—indicated drugs listed in the background section.

In some embodiments, a device as described herein is free of a stored electrical energy source. That is, the device is not powered by a battery or energy stored in a capacitor or other storage system. This does not prevent the device from being incorporated into another device that does rely on stored electrical energy. For example, such devices may be deployed along with or as part of a pacemaker device. While the pacemaker itself would rely on battery power, the delivery device would not need to feed off of that power supply, but instead, would operate in response to an external stimulus.

Assembly of Externally Stimulated Drug Release Devices

Reservoirs may be made from any materials for example (but not restricted to), etched silica wafers, or made from polymers such as PDMS (or PCL, PLGA, EVA, PMMA or poly anhydrides). Polymer based reservoirs may be made with any suitable technique, including cast or extrusion molding.

Membranes may be manufactured from numerous polymers for example, PLGA, PDMS, PMMA, hydrogel, EVA or PCL. Magnetic membranes may be made by suspending iron containing particles such as ferric oxide. Magnetite may also be used.

Gold nanoparticles may be made by covering silica cores with gold in many sizes.

The system may include a valving system such that flow is regulated and background leakage is minimized. Such valves may also protect against accidental release in the event of a non-triggering external stimuli. For example, these valves may be used to limit accidental release from physical manipulation, such as rubbing or pressure from surrounding tissues, where a magnetic stimulus is used to facilitate desired release. The valve may be a directional check valve, and combining with the magnetic membrane actuation, can regulate the amount of drug released at each pumping cycle.

A top view of an exemplary check valve geometry is shown in FIG. 10a. The valve chamber has a reverse channel width WR in the reverse flow direction (to the left as shown), and a forward channel width WF in the forward flow direction (to the right, as shown). The channel width transitions from the reverse channel width to the forward channel at an angle. As depicted, the forward channel appears funnel-like and the reverse channel is substantially tubular. The dimensions for the channel, transition angle, retaining and support pillar size, gap spacing can vary.

Two sets of small square pillars confine microspheres within the valve chamber. The microsphere inlet channel is closed off once microspheres are injected. Therefore, in FIG. 10a fluid flow is to the left and right. The gap spacing between the pillars is smaller than the diameter of the particles. Support pillars are used structural supports to prevent channel collapse.

FIG. 10a shows the microspheres collecting at the retention pillars forming porous media. The porous media lengths are represented as LR and LF respectively (where R is reverse and F is forward). The ratio of resistance, between porous media formed in the reverse and forward direction, is the working principle behind the check valve. The porous media resists diffusion by increasing the drug particles' path length and complexity (tortuosity) as shown in the left hand portion of FIG. 10c, where microparticles gather in the narrow reverse channel of the valve. When flow moves from right to left, as depicted, the micropores essentially block the narrow reverse channel, resulting in a blockage of flow in that direction. The right hand portion of FIG. 10c depicts the opposite situation, where flow is permitted left to right, forcing the microparticles against the retention pillars in the forward channel thereby facilitating flow in that direction.

The release system may be constructed in a variety of ways from single to multiple reservoirs, with and without microchannels and valves, requiring various stimulus for activation.

Reservoir

A reservoir may be made of any suitable material and is essentially a housing or container for holding the supply of the deliverable material. Typically, the reservoir has an open portion to facilitate loading of the deliverable. The opening can be sealed by the membrane.

A silica chip may have a reservoir etched into the surface. A drug such as, but not limited to, paclitaxel or docetaxel may be loaded into the reservoir by pipetting a concentrated drug solution in ethanol into the well followed by nitrogen gas blowing to dry the contents followed by repeat administration until the well is almost full of drug (or contains a desired amount). The reservoir may then be covered with a thin porous magnetic PDMS membrane using a spinning method, (see examples below), or may be covered with a porous magnetic PCL, PMMA, PLGA or EVA membrane.

In a single reservoir with puncture system this device would be adapted to include a non-porous membrane with a membrane puncture device that can be impacted by the membrane upon actuation.

In a single reservoir with microchannel system the device would include a non-porous membrane lying above one or more micro channels containing dissolved drug to allow water flow under a pumping action.

In a single reservoir in a bilayer sandwich-type assembly a thin PDMS disc (e.g. 1 cm in diameter) with a drug filled reservoir (e.g., 0.5 cm diameter and 1 mm deep) might be covered with a thin elastic or brittle polymer membrane. In the region of the reservoir, a "washer or doughnut" shaped (e.g. 0.48 cm outer diameter and 3 mm thick) loaded with magnetic particles might be assembled and surrounded by another 2 mm thick non-magnetic ring of polymer to hold the washer in place over the reservoir. Upon application of a magnetic field the large mass of magnetic material in the thick washer above the thin membrane covering the drug filled reservoir would be subjected to a large force. This would allow for fracture of the thin film and drug release.

A single device could be made with multiple reservoirs. The additional reservoirs could contain additional identical drug, or could contain additional therapies. The additional reservoirs could be configured for simultaneous or separate release of their contents.

Dose Control of Proposed Systems

In order to control either or both the timing and size of dose, a device might be actuated with a magnet a number of times to give repeated small unit doses, or a stronger magnetic field might be applied or a magnet might be brought closer to the device.

In some cases a series of reservoirs might be etched into a single silica wafer or molded into a single polymer construction. Reservoirs of different sizes and configurations could be used to achieve different release profiles. For example, if the reservoirs had different widths then the widest width reservoirs would allow the greatest magnetic deflection of a magnetic polymer covering. Therefore, at a lower magnetic applied field the widest aperture reservoir might allow sufficient membrane deflection to cause drug release form that reservoir whereas other reservoirs might retain their drug due to insufficient magnetic deflection. Subsequently, a higher magnetic field might be applied to release drug from remaining reservoirs. In this manner, a device containing multiple deliverables could be made such that the release of each was selective, based on the strength, as well as placement, of the external stimulus, or magnetic field.

The time of stimulation of a porous magnetic membrane over a drug reservoir might allow for control of dose. In some embodiments, as water enters a reservoir containing a deliverable, e.g. drug, the drug concentration might rise and lots of drug might be released. In such a case the initial time of magnetic stimulation of the membrane might be short to give a required dose and the subsequent duration of magnetic stimulation might be extended to maintain that dose as the drug became diluted. However for water insoluble drugs like paclitaxel or docetaxel, the water in the reservoir might be saturated with drug so that the membrane pumping might allow a fixed dose of such dissolved drug to be released through the porous membrane during a fixed time. This would allow more water to enter the reservoir, dissolve more drug ready for a second pumping at a later time.

Gold Systems

Gold nanoparticles might be included into heat sensitive membranes (e.g. made from PCL) covering drug loaded reservoirs so that when near infra red light was shone on the membrane the gold undergoes plasmon resonance, heated and melted or distorted or vibrated the membrane to release a drug underneath. The gold nanoparticles may be manufactured using methods that control the size of the particles. Smaller particles require different wavelength light for resonance allowing control of which reservoir covering melt.

Therefore it might be possible to selectively release drug from a series of reservoirs by covering the reservoirs with membranes containing different sizes of gold nanoparticles. Such membranes might also be manufactured from other polymers with glass transitions or melting points below temperatures reached by the resonating gold. In some applications gold nanoparticles might be included in a drug filled polymer (no reservoir). Upon application of the appropriate wavelength light, the polymer might become more flexible due to internal heating (glass transition) or even melt to release drug trapped in the polymer. A suitable polymer for this might be, for example PCL. Such a polymer system might be used to coat medical devices such as orthopedic implants, catheters or stents to release drug at required times to prevent bacterial growth or unwanted tissue reactions.

Magnetic Systems as Pumps

In some aspects magnetic membranes might be used as pumping diaphragms. In such a system a capillary tube might run through the membrane from the external face of the device into the drug filled reservoir. When a magnetic field is applied, the membrane may deflect and water might circulate in and out of the reservoir via the capillary tube. Such a system might not require pulsing of the magnetic field but simply a single deflection of the film under a constant magnetic field to deflect the membrane to allow a fixed volume of water to enter the reservoir, dissolve a fixed amount of drug and when the magnetic field is removed the membrane might pump out a fixed volume of water containing a fixed dose of drug. This pumping system might alternatively be affected by channels running under the membrane. In an example of this, two PDMS blocks with reservoirs (filled with dry drug) and channels might be connected via a thin magnetic film between the reservoirs. Upon application of a magnetic field the magnetic membrane could deflect in one direction and draw water into one chamber whilst squeezing air/water out of the other chamber. Drug may dissolve in the water so that when the magnetic field was removed the membrane would return to the original position and pump drug out of that reservoir. At the same time the other reservoir could then take in water so that when this was compressed by the second application of a magnetic field, the drug could be pumped out of this chamber.

In some aspects, a film may be punctured with a fine laser beam to introduce one pore or multiple pores. This may be done to a magnetic film or a non magnetic film. In some cases, a second magnetic film may pump the drug through the hole in the non-magnetic membrane.

In some applications a magnetic film may be simply joined to a non-magnetic film with drug contained in the capsule-like device. A laser hole may be pre-cut in the non-magnetic membrane. When placed in the body (e.g. with the nonmagnetic film laid against the back of the target organ e.g.: the eye ball) the application of an external magnetic field would pull the magnetic membrane against the drug (with or without any influxed water) to extrude some drug onto the organ tissue.

In brachy therapy, multiple rice seed sized implants are squeezed through needles into the prostate at multiple sites in the prostate using a technique called fenestration. Such a method might be used to place similar sized silica chips containing single drug loaded reservoirs in the prostate or any tissue. The membrane could be a porous magnetic membrane or one containing gold nanoparticles or a combination of both. A strong magnet or a light source probe might be introduced into the urethra or rectum via a catheter to stimulate release of drug.

Design and Microfabrication of Drug Storage Reservoirs and Magnetic Valves

Drug reservoirs are to be formed in a polymer substrate and may have a physical volume of for example 6.6 µl which could load suitable amounts of as desired deliverable. For example, such a volume would allow loading of approximately 125 µg of latanoprost and 2.5 mg of timolol into the reservoirs as dry material. Each reservoir can be made to any suitable volume. For example, a reservoir may have a volume of 1 µl, 2 µl, 3 µl, 4 µl, 5 µl, 6 µl, 7 µl, 10 µl, 15 µl, 20 µl, 25 µl, or ranges between any of these values. In some embodiment, the device would hold enough drug to treat the disease for up to about three months. Other examples of suitable treatment times include about 1 week, about 2 weeks, about 3 weeks, about 1 month, about 2 months, about 3 months, about 4 months, about 5 months, about 6 months, and ranges between any two of these values.

For example, it is known that patients treated with typical anti-glaucoma drug combination, such as latanoprost with timolol (under the brand name, Xalacom, require a therapeutical dose of 1.6 µg/day and 75 µg/day, respectively. These amounts are dispensed in a single eye drop with considerable wash off and only 1 to 7% ocular availability. The solubility of latanoprost and timolol are 50 mg/ml and 2.5 mg/ml, respectively. Therefore, upon activation of the magnetic valve, water in the form of tears from the surrounding may enter the reservoir. The valve can then close to allow proper retention time and there will be 0.33 µg and 16.5 mg of latanoprost and timolol drug dissolved locally in the reservoir. The dissolved amount is limited by the maximum solubility of each drug. When the magnetic valve is actuated again to open, 0.33 µg of latanoprost and 16.5 mg of timolol may be delivered. By repeating the magnetic cycle 5 times, the total drug delivery will reach the target daily dose (as defined by the eye drop dosage). However, because the efflux drug volume is small, eye drop wash off (wastage) will be eliminated, so that it is likely that fewer actuation cycles will be needed to attain therapeutic levels of drug in the eye. The number of actuation cycles can be programmed and controlled externally. Because there is limited wastage, less actual drug is needed, thus requiring smaller amounts of drug to be stored in the device than would be required for the same number of doses via the traditional eyedropper delivery.

Drugs are loaded into the reservoirs and the sealing process may be accomplished by transferring stacking layers of polymers using a flip-chip bonder. Firstly, a PDMS (polydimethylsiloxane) layer may be formed by a micro-molding technique and will serve as a master. Materials commonly used in ophthalmology such as hydrogels and PDMS may be spun-cast using the PDMS master. Free-standing hydrogel/PDMS membranes containing magnetic nanoparticles (about 10 nm in diameter) in the matrix will be formed using micro-molding and spin-casting techniques. The hydrogel membrane may then be transferred and sealed with the porous layer using flip-chip bonding. Under a rotating magnetic field, the magnetic membrane will rotate in a desired direction, when the magnetic field is aligned with the dipoles of the nanoparticles.

The magnetic valve may slide against the sealing. For example, a magnetic field of 500 mT can generate 150 Pa on a PDMS magnetic membrane incorporated with iron oxide particles. This approximates a $3 \times 10^{-3}$ NT magnetic force on a 5-mm diameter valve. While increasing the magnetic field will increase the corresponding magnetic force, soft contact friction between two polymer surfaces may greatly decrease in the presence of water. This is particularly advantageous since tear films are readily available in the conjunctival cul-de-sac so that surface dry out should not be an issue for most patients.

One of the challenges could be that the magnetic membrane may come into contact with the adjacent porous membrane when implanted and thus, be under pressure exerted from the surrounding tissue in the conjunctival cul-de-sac. This contact problem can be minimized if the porous membrane has a rigid or semi-rigid backing, with similar mechanical properties to a hard contact lens. However, this may cause discomfort in patients. The correlation between pressure from the surrounding tissue and magnetic membrane deformation can be addressed through manipulation of other properties of the device, or through modification of any micro channels used in the device.

Anticancer Applications

Controlled dosing of chemotherapy close to tumor sites or tumor resection sites is desirable to reduce drug toxicity. The implantable devices described herein may allow for accurate control of drug release. Such control may relate to dose amount, timing, or both. In some embodiments the placement of the dose may also be controlled.

For example, ovarian tumors are often discovered late and may be associated with seeding before or after resection. These metastatic sites are difficult to treat. In one embodiment, a drug loaded magnetic implant of the type described wherein can be sutured to the side wall of the cavity. Then the patient could easily bring a magnet up to the skin adjacent to the device and release as much drug as was required by actuating the device with the magnet for a defined number of times. This anticancer application is not limited to ovarian cancer but could easily be adapted to treat prostate or colon cancer (introduce magnet through anus), breast cancer (skin application of magnet), cervical cancer (vaginal introduction of magnet), etc.

Muscoskeletal Applications

There are numerous medical conditions where muscoskeletal tissues such as cartilage, tendons, meniscus or bone are damaged, removed or absent. For example in osteoarthritis, cartilage may be damaged or compromised and this is often followed by bone remodeling. Many conditions that might be treated with bone fusion, such as where discs are removed, or treatments for spine fixation might be assisted by improved bone regrowth. In other surgical situations large sections of bone may be missing e.g. following trauma or surgery (e.g. to remove bone tumors).

Cartilage treatment methods employing an implantable device disclosed herein could include proangiogenic agents (such as vascular endothelial growth factor: VEGF) or even agents that might stimulate local stem cells to differentiate into chondrocytes near the site. New methods are currently being developed to bridge bone voids and spaces. Methods include the placement of polymeric scaffolds into the void seeded with appropriate materials. An improved method might replace or augment these current methods. In some cases, stem cells should be encouraged to form osteoblasts to lay down new bone. Angiogenesis could be encouraged in a controlled and sequential manner. Any delivery vehicle for these agents could be degraded or incorporated into new bone to avoid the need for later extraction. The general device comprised a reservoir for containing active agent, covered by a membrane. Upon stimulation (by magnetic or light induced heat sources) the membrane would move to distort or melt and induce the release of the active agent in a controlled manner. These agents would include those that encourage differentiation of stem cells into osteoblasts (such as, e.g., BMP or PTH) or proangiogenic agents such as dexamethasone, ascorbic acid, glycerol phosphate or proangiogenic agents such as VEGF, transforming growth factor Beta or platelet derived growth factor or agent-specific tissue regrowth or repair agents such as insulin like growth factor or fibroblast growth factor. Agents that encourage bone growth such as bisphosphonates (e.g. alendronate or zolendronate) might be included. Because inflammation is associated with macrophage influx into damaged areas then anti-inflammatory agents might be included such as dexamethasone (or other steroids) (note macrophages may differentiate into osteoclasts and cause further damage to bone). Antibiotics might also be included in these systems.

Ocular Delivery Issues

There are numerous diseases of the eye. These range from focusing to the correct focal length to diabetic retinopathy to macular degeneration to infections. Corneal revascularizations the excessive in-growth of blood vessels in to the cornea, caused by a low reception of oxygen. One of the most common causes is contact lens wear, and to a greater extent, continued use of extended wear contacts. The condition could threaten one's eyesight and reduction of neovascularization has been achieved in rats by the topical instillation of drugs like triamcinolone or doxycycline.

Macularedema results from thickening and swelling of the macula and may distort a person's central vision, since the macula is near the center of the retina at the back of the eyeball. Macular edema sometimes appear for a few days or weeks after cataract surgery, but most such cases can be successfully treated with NTHE or cortisone eye drops.

By blocking VEGF-A in the eye, the drug ranibizumab may prevent and reverse vision loss caused by wet macular degeneration. The drug is injected intravitreally (into the vitreous humour of the eye) once a month. If monthly injections are not feasible, the regimen may be reduced to 1 injection every 3 months after the first 4 months. However, dosing every 3 months is linked to a loss of approximately 5 letters (1 line) in visual acuity for the following 9 months as compared with dosing on a monthly basis. Insertion of a device as described herein could facilitate more frequent dosing.

Diabetic Retinopathy

Highly fluctuating glucose levels and localized retinal hypoxia which can occur in patients with advanced type 1 and 2 diabetes can lead to an angiogenic response and the creation of disordered and unwanted, leaky capillaries in the retina. Eventually, this problem can lead to blindness. Almost 10% of the North American population has diabetes. After 20-25 years of disease, 50% of those with type 1 and 20% of those with type 2 diabetes will develop proliferative diabetic retinopathy and eventual blindness. Currently, there are a number of agents proposed for use against advanced retinopathy which are either FDA approved or in advanced clinical trials. These agents largely target the capillary growth factor VEGF to prevent angiogenesis in the retina. Some people develop a condition called macular edema. It occurs when the damaged blood vessels leak fluid and lipids onto them acula, the part of the retina that lets us see detail. The fluid makes the macula swell, which blurs vision.

As the disease progresses, diabetic retinopathy enters an advanced proliferative stage when blood vessels proliferate which can bleed, obscure vision, and destroy the retina. Fibrovascular proliferation can also cause tractional retinal detachment. The new blood vessels can also grow into the angle of the anterior chamber of the eye and cause neovascular glaucoma. Three treatments are available for diabetic retinopathy: laser surgery, drugs and vitrectomy. A commonly used drug is Triamcinolone which is a long acting steroid preparation. When injected in the vitreous cavity, it decreases the macular edema but the effects of triamcinolone only last up to three months, which necessitates repeated injections. Complications of intravitreal injection of triamcinolone include cataract, steroid-induced glaucoma and endophthalmitis. Newer drugs to treat diabetic retinopathy include kinase inhibitors and anti angiogenic compounds.

The localized treatment of diabetic retinopathy using combination therapy for the treatment of ocular neovascularization has been suggested by several researchers. (De la Cruz J P. Et al 2004 *Diabetes Metab Res. Rev.* 20, 91-113 or Speicher M A., et al. 2003 *Expert Opinion Emerg. Drugs.* 8, 239-50) but must be given by regular intraocular injection with associated risk of retinal detachment, hemorrhage and patient morbidity (Myles M E et al 2005. *Advanced Drug Del. Rev* 57, 2063-2079. Recently, Dr Burt's group at UBC has identified the antiproliferative, anticancer agents DOX, camptothecin and antisense oligonucleotides to bcl-xl as powerful antiangiogenic agents, particularly if used in combination (Jackson J K., Gleave M E., Gleave J., Burt H M. 2005. Angiogenesis: 9; 273-279). The proliferative aspects of angiogenesis represent an attractive disease target since antiproliferative drugs have been reported to inhibit capillary cell growth at much lower concentrations than, for example, tumor cell proliferation. Therefore, toxicity issues associated with the use of higher concentrations may be reduced. This is particularly desirable for treating retinal tissues where any background localized drug toxicity (acceptable in cancer therapy) could compromise ocular function. In this study (Jackson 2005) these agents were proposed as antiangiogenic therapies for the treatment of diabetic retinopathy. However, without adjunct control on fluctuating glucose levels and hypoxic conditions these agents must be continuously administered to prevent progressive angiogenesis.

This situation represents an unusual drug delivery issue. For treatment of diabetic retinopathy, the drug can desirably be antiangiogenic, administered as infrequently as possible, delivered as close to the retina as possible and released in a controlled manner to maintain therapeutic levels. Unfortunately, intraocular polymeric or other drug delivery devices may obscure vision, damage the retina or induce an inflammatory response despite offering the optimal location for controlled release of the drug. Bock F et al (2007 *Invest Opthamol Vis Sci* 48, 2545-52) proposed that antiangiogenic drugs might be administered topically to the anterior segment of the eye to treat diabetic retinopathy. The clear advantage of a MEMS device as described herein for this application is the ability to release the drug on demand on this surface. Diabetic retinopathy is particularly suited to MEMS therapy as ocular examination by a physician can qualitatively determine the level of angiogenic progression and the need to increase the local concentration of drug(s).

Age Related Macular Degeneration

This causes vision loss due to abnormal blood vessel growth (choroidal neovascularization) resulting in similar issues to retinopathy. The disease may be treated using the same antiangiogenic drugs as used for retinopathy and may be injected directly into the eye every few weeks. The cost of these drugs is high at approximately $150 to $2000 per treatment. Other treatments include the use of photodynamic therapy.

Glaucoma

This is a chronic ophthalmic disorder and is associated with elevated intraocular pressure (TOP). Long-term high IOP will cause irreversible optical nerve damage and subsequent vision loss and blindness. It is also suspected that the fluctuating IOP is an independent risk factor on its own that contributes to glaucoma progression. According to The Canadian National Institute for the Blind (CNIB), glaucoma is one of the most common causes of blindness and affects 250,000 Canadians. Although it often occurs in older people, it can develop at any age. According to The National Coalition for Vision Health, at least 300,000 Canadians are affected with glaucoma (http://www.visionhealth.ca/data.htm) that is almost 1% of Canadians are affected by this disease.

Most intervention in glaucoma treatment has focused on lowering the IOP. All these drugs have undesirable side effects that must be monitored. Failure of patients to comply with dosing is a huge challenge with glaucoma treatments. Drugs include prostaglandin analogs, beta adrenergic receptor antagonists, alpha 2 adrenergic antagonists. A number of drugs are used to reduce IOP including pilocarpine, beta blockers (e.g. Timolol) and prostaglandin analogues (e.g. Latanoprost). However, these drugs are usually supplied as eye drops which only allow approximately 1 to 7% of the drug to reach the target site, the aqueous humor (i.e., the thick watery substance that is between the lens and the cornea), while the rest is washed away by tear drop and potentially drains into the nose through the puncta, the tear duct that links the eye to the nose. Thus the majority of the drug may be absorbed systemically with associated side effects. Although topical-delivered prostaglandin drugs produce much less systemic side effects compare to beta blockers, patient compliance is still the most unpredictable barrier. Failure in glaucoma intervention due to patient non-adherence was reported to be unacceptably high at around 24 to 59%. A sustained drug release system using an ocular insert may improve patient compliance and reduce systemic toxicity since less drug is used and less tears are generated. Clinically proven sustainable drug release ocular devices, such as Ocusert™ first appeared in the 1970's and used a diffusion membrane to control drug release from a drug reservoir. The device has an elliptic shape with the longer axis of 13 mm and thickness of 0.2 mm. The device is implanted in the conjunctival cul-de-sac, or the bottom of the eye to release pilocarpine for up to a week. Ocusert was successful through the 1990's until newer, more effective topical drugs, such as prostaglandin analogues came to market. The increased cost of Ocusert, including weekly surgical replacement, may also have played a role in its reduced popularity to newer drugs in the eye drop formulation. Other ocular drug delivery devices such as drug-coated contact lens, muco-adhesive inserts, injectable hydrogel-based pastes and biodegradable compounds are also being developed. More recently, products containing a small tablet of drug (e.g., Vitrasert (from Bausch)) have been developed for surgical placement in the eye. These devices are mostly based on polymer-eluding drug delivery. Furthermore, the supporting organization, QLT, has been developing a polymer-based drug delivery device to be surgically inserted into the punctum to provide sustained drug release up to three months.

Ocular treatment of glaucoma represents an unusual drug delivery issue. For first-line treatment of glaucoma, the drug should arguably be timolol or a prostaglandin analogue (e.g., Latanoprost), administered daily as a unit dose and delivered as close to the anterior chamber as possible and to be released in a controlled manner to maintain therapeutic levels. Although intraocular placement of a drug delivery device might offer greater drug availability, this method may obscure vision, damage the retina and/or induce an inflammatory response. A MEMS device loaded with anti-glaucoma drug such as prostaglandin-based drug, can be surgically placed in the conjunctival cul-de-sac of the eye to release drug up to three months. The clear advantage of a MEMS device for this application is the ability to release the drug in a controlled pulsed concentration. Glaucoma is particularly suited to MEMS-based therapy, as daily unit doses of drug are required and ocular examination by a physician every three months may qualitatively determine the level of glaucoma progression and the need to increase the local concentration of drug(s).

Focusing Issues

In focusing (myopia etc) the muscles that contract the lens-distortion muscles may no longer function properly. This is often corrected by contact lenses or glasses. However, in people with bifocal needs these devices do not respond to different focusing needs. Laser surgery may correct some of the lens defects but not all people want laser surgery and it does not address all focusing needs. What is desired is a contact lens of variable thickness whereby the thickness is flexible depending on the focusing need and driven by an external stimuli. In other eye diseases, drugs may preferably be delivered to the eye in a controlled manner. However drugs rinse away very quickly and do not attain reasonable concentrations in the eye. This situation may be better treated by having a controlled release formulation of the drug close the eye. Optimally the drug might be held on the eye to improve uptake rather than getting washed away and be released on demand so that the patient does not have to use a dropper repeatedly.

Methods to Treat Eye Disorders 1

A flexible contact lens may be used to deliver drugs to the eye or to correct for focal length. For drug delivery, the drug may be held in a reservoir in the lens that also contains magnetic particles. An externally applied magnetic field may then distort the lens to release drug through small apertures. Only a small amount of drug might be needed as the lens would hold the drug on the eye ball for some time, increasing the chance of tissue uptake. This external field might come from a magnetic system embedded in eye glasses. For focal length adjustment, the lens may contain a small circular magnetic or solenoid coil which contracts when an external stimuli is applied. This contraction might then adjust the focal length. In advanced systems drug release or focal length adjustments might be further controlled by a second or alternative stimuli such as finger rubbing the closed eyelid or simply by the closing of the eyelid in a coded manner (e.g., an extended blink might allow a 50 um lens adjustment and a 2 second blink might reset to original dimensions).

Methods to Treat Eye Disorders 2

A drug reservoir can be sealed by a magnetic membrane. Magnetic membranes can either function as a rotating valve or as a pumping diaphragm. A magnetic valve has a pin that fits into a slot on the sealing layer. When an external magnetic field is rotating, the magnetic valve can also rotate and slide against the sealing layer. When the hole(s) on the magnetic valve matches the hole(s) on the sealing layer and the cap, drug will diffuse out.

For a pumping diaphragm system a magnetic membrane serves as a pumping diaphragm that pumps the drug out from the reservoir though a pore under an external magnetic field. This device may be constructed in any shape.

For behind the eye applications to treat retinopathy or macular degeneration, the shape of this device might be similar to a small contact lens. For implantation inside the eye or on the sclera, the device might include an injection needle or an anchor connection to prevent it floating in the vitreous humor. For in front of the eye drug delivery, the MEMS device dimension could be an elliptic-shape disk, (13 mm×6.5 mm×0.2 mm) to be implanted in the conjunctival cul-de-sac for the treatment of e.g. glaucoma.

EXAMPLES

Example 1

Construction of an Elastic Polymer Membrane Containing Uniformly Dispersed Ferric Oxide Particles PDMS (Sylgard 184 Silicone Elastomer, Dow Corning Corporation) was used as the polymeric matrix. PDMS was supplied in two compounds: a pre-polymer and a cross linker (or hardener). Typical mixing ratio of pre-polymer and cross linker is 10:1; however, a 5:1 ratio was used to achieve a greater link formation in the polymer. This led to a more rigid polymer with reduced liquid absorption. Magnetic PDMS composites were prepared by using two types of coated iron oxide particles as filler materials. The coated particles (Ferro Tec, MA, USA) were: (1) EMG1200, proprietary fatty acid-coated iron oxide nanoparticles; and (2) EMG1400, iron oxide nanoparticles with a proprietary hydrophobic surfactant. Both were obtained as dry particles. The weight percent of iron oxide in EMG1200 and EMG 1400 were 67.2-72.6% and 77.0-83.0%, respectively. The particles were a 50/50 mixture of $Fe_3O_4/\gamma$—$Fe_2O_3$ with an average particle size of 10 nm.

Colloid dispersions of EMG1200 and EMG1400 particles were made separately to form the ferrofluid by dissolving dry particles in toluene (Fisher Scientific, ON, Canada), a compatible solvent for the dry particles. Successive additions of particles into toluene were followed by stirring, heating at 35° C., and sonication in an ultrasound bath (Kell-Strom, Branson Model 1510), that was necessary to achieve a stable colloid. The final ferrofluid was dispersed by sonication for 30 minutes. The PDMS pre-polymer was dissolved in toluene and stirred for 10 minutes to achieve a thin polymer base. The ferrofluid was then mixed with the polymer base at a mass fraction of 40% w/w particles to the polymer. This was then sonicated for 10 minutes using a high-power sonic tip (Misonix Incorporated, XL2020, NY, USA) and followed by sonication in a sonic bath at 35° C. and stirring for 30 min. The composite solution was then stirred for 3 hours under a fume hood to allow the toluene to evaporate and then degassed in a desiccator for another 60 minutes. The cross linker of PDMS was then added and mixed fully for 15 minutes followed by degassing for 30 minutes. The PDMS magnetic membrane was formed by spin-coating the composite on a sacrificial layer (e.g PAA or photo resist AZ 4110) on a glass substrate and cured at 80° C. Free-standing magnetic PDMS membranes were fabricated using a combination of micro-molding, sacrificial etching, and bonding techniques described in the next section.

Example 2

Construction of a Device Comprising a Magnetic Polymer Membrane (with a Pore) and a Reservoir Containing a Drug (Docetaxel)

The fabrication process for the drug delivery device is described in detail in steps.

Step 1: drug reservoirs were made by molding PDMS from photo resist structures using standard photolithography. A layer of SU-8 2150 (MicroChem Corp., MA, USA) photo resist was spin-coated on a previously cleaned (piranha etch)

silicon substrate in two spinning steps (500 rpm for 10 s and 1400 rpm for 50 s) and patterned as pillars in different sizes (Ø 3-6 mm). The photolithography process was followed according to manufacturer's guidelines. The height of the pillars was measured to be 480 to 580 µm using a Wyko surface profiler (VEECO MetrologyGroup, AZ, USA).

Step 2: PDMS (Sylgard 184 Silicone Elastomer, Dow Corning Corporation) was prepared with a mixing ratio of 5:1 (pre-polymer to cross linker), poured on the SU-8 patterned silicon substrate, degassed for 30 min, cured at 80° C. in a convection oven, and peeled away from the mold. Step 3: the SU-8 transferred features into PDMS created cavities that were then ready for loading with the drug. Prior to drug loading, the reservoir layer was treated with oxygen plasma for 20 seconds (100 m Torr pressure, 30 W power, and at 20° C.). Drug could be loaded in two ways: (1) as a powder where the amount of drug in the reservoir was determined by weighing it before and after drug loading, (2) as a solution where drug was dissolved in a volatile solvent and then the solution was deposited in the reservoirs using a pipette. Using method 2, docetaxel (DTX) loading was performed after treating the reservoir layer with oxygen plasma and before permanent bonding of the reservoir layer to the membrane layer. A mixture of 3H-DTX and unlabeled DTX at the desired concentration of 20 mg/ml was prepared in a 50/50 solution of ethanol and dichloromethane (DCM). In each deposition cycle, 5 ml of the drug solution was deposited into a reservoir by a pipette and dried by evaporating the solvents. Deposition and drying process was repeated until the desired nominal drug content (e.g. 200 mg) was achieved. Leaving a thin layer of a water-soluble polymer as a coating to the content of the reservoir was optional.

Step 4: an aqueous solution of poly (acrylic acid) (PAA) was used as a water-soluble sacrificial layer material. PAA was purchased as powder (Mw=1800, Sigma-Aldrich, Canada) and was mixed with distilled water to achieve a concentration of 20% w/v. It was heated for 10 minutes in a 90° C. water bath to promote dissolution and was then filtered (4.5 mm pore size, Millipore Corp., MA, USA). After a glass substrate was cleaned with organic solvents (e.g. IPA and acetone), it was treated with air plasma for 2 minutes prior to coating to help improve the wet ability of the glass substrate which was found to be an important step for achieving a uniform coating of PAA solution on the glass substrate. PAA solution was dispensed onto the glass substrate until about 90% of the surface was covered with the solution and then spin-coated in two spinning steps (500 rpm for 10 seconds and 1000 rpm for 20 seconds). It was cured at 150° C. on a hotplate for 5 minutes. The resulting sacrificial layer has a typical thickness of about 8 µm. The magnetic PDMS membrane was formed by spin-coating of the prepared composite (described in previous section) on the sacrificial layer in three spinning steps (500 rpm for 15 seconds, 1000 rpm for 15 seconds and 2000 rpm for 30 seconds) and cured at 80° C. The fabricated membrane has a thickness of about 40 to 45 µm.

Step 5: After the magnetic membrane was cured, it was treated with oxygen plasma (100 m Torr pressure, 30 W power, and at 20° C.) for 20 seconds, and was irreversibly bonded to the reservoir layer that was previously treated with oxygen plasma.

Step 6: The device was detached from the substrate by dissolving the sacrificial layer in a DI water bath.

Step 7: the aperture was created by a laser ablation process using either carbon dioxide laser or UV laser. The UV laser used was a pulsed Nd: YAG laser system, Quick laze (New Wave Research, Sunnyvale, Calif.). For example, an aperture of 100×100 mm$^2$ was ablated with Quik laze laser system using UV light pulses at 5 Hz (355 nm wavelength) with 0.11 mJ(70% low) and a speed of 5 µm/s. (See FIG. 2-b). The carbon dioxide laser, XL-9200 (Universal Laser Systems Inc., Scottsdale, Ariz.), has a characteristic wavelength of 10.6 mm, and the infrared laser operates with variable settings for power, speed, and pulses per inch (PPI). For example an aperture of ~Ø120 µm was ablated with carbon dioxide laser system using IR with settings of 3% power (~1.8 w), 5% speed (12.7 cm/s), and 500 PPI.

Step 8: The device was exposed to a 40 mg/ml bovine serum albumin (BSA, Sigma-Aldrich Canada Ltd., Ontario, Canada) solution in phosphate buffered saline (PBS) and incubated at 37° C. to increase the wet ability of the magnetic PDMS membrane and thus filling of the drug reservoir with water. The hydrophilic aperture walls results in surface-tension driven flow through the aperture and gradual filling of the reservoir with solution. The solution dissolves the solid DTX inside the reservoir up to its saturation solubility (about 5 µg/ml) (See FIG. 2-b for SEM of the device cross section).

Example 3

Use of a Magnet to Actuate the Device of Example 2

Methods and Materials:

The force on the membrane was induced by a mechanically moving cylindrical NdFeB permanent magnet (with a diameter of ½" and a thickness of ¾", D8C, K&J Magnetics, Inc., PA,USA). The magnet was mounted on a computer controlled motorized stage (an ATmega 328 microcontroller on the Arduino Duemilanove board, by Arduino, Italy). The distance between the magnet and the device was adjustable. The MEMS drug delivery devices were placed in 20-ml glass scintillation vials individually and actuated in 4 ml of an aseptically filtered solution of 1% w/v BSA in PBS (pH 7.4) (referred to as BSA solution subsequently).

One actuation cycle is defined as a combination of two intermediate events, discharge (with magnetic field) and mixing (without magnetic field, membrane relaxes and solution refills the reservoir). Each actuation cycle is controlled by two time constants associated with these two events: (1) a discharge time (td) of 100 seconds which is required for complete release of the displaced volume in the reservoir when membrane deflects; and (2) a mixing time (tw) of 200 seconds which is required for drug mixing with the pumped-in solution. Detailed experiments and simulations that lead to the selection of these two time constants are addressed in Section 3. At each measurement data point (i.e. after actuation cycles and no-actuation periods) the solution was removed and analyzed for DTX or TB content and replaced with a fresh 4 ml aseptically filtered BSA solution for the consecutive actuation and no-actuation periods.

Solutions for tritium-labeled DTX content measurement were subjected to drug extraction steps. One ml DCM, which is a water immiscible hydrophobic solvent, was added to the solution and vortex mixed in order to selectively dissolve and extract DTX in DCM. Interaction of the protein molecule with organic solvent (DCM) led to the protein's precipitation at the aqueous-organic interface. After allowing the organic and aqueous phases to separate for 10 minutes, the aqueous interface was aspirated out and the remaining organic phase (which contains the released drug from the device) was transferred into scintillation vials, filled with CytoScint liquid scintillation fluid (Fisher Scientific, Fair Lawn, N.J.). Disintegrations per minute (DPM) were measured using a LS 6500 series, multi-purpose scintillation counter (Beckman Coulter, Inc., Brea, Calif.). A standard curve for converting DPM values to DTX content was created by introducing various volumes from drug stock solution (20 mg/ml) into 4 ml of 1% BSA solutions in PBS and following similar drug extraction steps. The measured DPM values for samples were always 100 times higher than the detection limit.

FIG. 3 shows the discharge of model drug (dye) over time as a small visible bloom when the device was actuated with a 176 mT magnetic field.

Controlled Release Study

Controlled release studies were performed using devices that had a membrane diameter of 6 mm with a nominal thickness of 40 µm, an aperture of 100×100 µm$^2$, and a nominal reservoir depth of 550 µm. Due to the low aqueous solubility of DTX, only a predefined amount of solid DTX may be dissolved (up to its saturation solubility) in the reservoir in each actuation cycle. This would have dual impacts on the device operation: (1) constant concentration of DTX solution will be available for delivery in the reservoir, thus the concentration of the drug solution will not decrease with time as might occur with other more soluble drugs; and (2) solid form DTX (biologically active) will be maintained in the reservoir for extended periods of time.

Effects of Number of Actuation Cycles and Magnetic Field

The amount of drug released was demonstrated to be controllable by adjusting two parameters: (1), number of actuation cycles; and (2), the distance of the permanent magnet from the device and thus the size of the magnetic field strength and gradient. The amount of released DTX from a device under 255 mT magnetic field was found to follow a linear relationship with the number of actuation cycles so that as the actuation cycle number increased the amount of released drug increased in a proportional amount as shown in FIG. 4-a. A similar relationship was observed for the amount of drug released as a function of magnetic field strength (FIG. 4-b). The amount of released DTX reported at a specific magnetic field represents the release after ten consecutive actuation cycles for all points. The magnetic field values were experimentally obtained with respect to distance. Linear DTX release profiles with respect to magnetic field and the numbers of actuation cycles allows for highly controlled on demand dosing.

Long-term, On-demand Release Profiles

In all controlled release experiments, each actuation mode consists of three actuation intervals and each actuation interval includes ten consecutive actuation cycles (FIG. 5). In the no-actuation periods, the device was left in BSA solution and thus drug release is uncontrolled and is expected to occur via background diffusion through the 100×100 µm$^2$ laser-drilled aperture.

Constant DTX release from a device using a 255 mT magnetic field is demonstrated in each actuation cycle. Serial cumulative release of DTX with and without magnetic actuation is shown in FIG. 5. The slope of the cumulative release curve is a quantitative measure of the release rate. A constant release rate of 171.7±16.7 ng per actuation interval (3.4 ng/min release rate) was achieved by magnetic actuation for 13 intermittent releases over 13 days. These release rates are shown in FIG. 5-b. For the device used in FIG. 5-a. Each data point is the average of the release rates for three consecutive actuation intervals. Drug release during no-actuation period was measured to be 0.053±0.014 ng/min at the end of each period. A 64-fold increase in DTX release has been achieved by magnetic actuations compared to no-actuations. This shows the low level of background diffusion from the device in the "off" state.

The long-term operation of the drug delivery device was investigated and the device used to collect the data shown in FIG. 5 was left in BSA solution for 22 more days and actuated once more with the same conditions. The results showed that the release rate remained constant at 160±10.2 ng per actuation interval which illustrates the consistency of the release rate over 35 days of device operation. The release from the same device after 8 months was also accurate with similar release rate. Furthermore, similar experiments for three other devices were performed using a 213 mT magnetic field over 6 days and found that 129±32.3 ng of DTX was released per actuation interval. This amount is in agreement with the prediction provided from data shown in FIG. 4-b.

The released drug from the device was tested with HPLC after 8 months that was encapsulated inside the device. The HPLC results show that over about 95% of the drug remained intact.

The drug release experiments further suggest the following: (1) the process of drug release can be "switched off" by removing the magnetic field and re-activated by re-applying the magnetic field, and (2) the resulting constant release rates are in line with the predicted values from simulation determinations for the required mixing time and the calculations for complete discharge of displaced volume after membrane actuation. The on-off switchable controlled drug release, may allow fine-tuned control of drug doses administered from implanted devices. Furthermore, no clogging of the aperture was observed throughout the experiments following examination of the devices using an optical microscope.

Example 4

Use of Device to Release Docetaxel to Kill Angiogenic and Proliferating Cells

A prototype device was actuated at the desired number of actuations in 1% BSA solution. The released DTX was extracted in 1 ml DCM, as described previously. This mixture was dried down under nitrogen flow at 40° C. and was then reconstituted in either HUVEC and PC3 cell media to the original volume of 4 ml. Alternatively, fresh solutions of free DTX were prepared in various concentrations (2-250 nM) in acetonitrile, dried down under nitrogen flow at 40° C., and reconstituted in cell media.

PC3 and HUVEC cells were seeded in 96 well plates in their respective media at a concentration of 1500 cells per well. The cells were allowed to equilibrate for 2 days at which time they became approximately 50% confluent and were ready for drug incubation. Cells were incubated for 2 days at 37° C. with 200 µl of either freshly prepared solutions of DTX at various concentrations or with the drug solution released from the device under various number of device actuations. Cell viability was determined using a CellTiter 96 AQueous Non-Radioactive Cell Proliferation Assay (MTS assay, Promega Corporation, Madison, Wis.) and quantified by reading the absorbance at 492 nm minus the absorbance at 610 nm using a spectrometric plate reader. In both experiments, the values presented are for the averages of six replicas for each condition.

Experiment

The biological activity of the DTX released from a device was investigated. This was achieved by incubating cells with the released drug in cell culture media and measuring the drug induced inhibition of proliferation in comparison to the inhibition caused by freshly made drug solutions. The device used for this study had been fabricated and left in BSA solution for two months (with an open aperture) prior to the experiment. The amount of DTX release during this period was estimated to be about 4.5 µg based on measured DTX diffusion rate. It was then actuated under a 255 mT magnetic field for different numbers of actuation cycles. The amounts of released drug were then experimentally interpolated from "number of actuations" to "drug concentrations", using FIG. 4-a.

Taxanes are antiproliferative drugs mainly used for their anticancer and antiangiogenic effects. Unwanted proliferation of capillary cells in the retina (angiogenesis) is responsible for compromising retinal function resulting in vision loss. Therefore, we used endothelial cells (HUVEC-capillary cells) in these proliferation studies, as these cells would be the target cells in the retina for treatment with docetaxel and therefore directly related to any clinical application of this system. PC3 prostate cancer cells were used as another representative example of a diseased cell line that might be treated using a docetaxel controlled release system described in this patent. The cell viability for both cell lines were studied when the cells were incubated with either the freshly prepared DTX at various concentrations or the DTX released from the device under various number of actuations. In both cases, the cell viability in the presence of released drug closely follows that of fresh free drugs as shown in FIGS. 6a and 6b. The cell viability equilibrated at about 34% for PC3 cells and about 24% for HUVECs, for both cell lines when they were either incubated with fresh free drug or incubated with the drug released from the device. The results confirmed that the antiproliferative effect of DTX was maintained over two months and the released drug from the device had approximately the same effect on cells as the freshly made drug solutions. This indicates that DTX does not degrade inside the PDMS MEMS device after two months.

Example 5

Methods to Prepare Porous Magnetic Membranes

Method for manufacture of magnetic porous PDMS membranes by including diblock copolymer and salt. 3 ml of PDMS was mixed with 20% w/w of diblock copolymer (40% PLLA and 60% MePEG total molecular weight 3330 D). 1% w/w of salt particulates with average particle diameter of 40 µm was then added. The cross linker was added and mixed for 5 minutes. The composite was spin-coated at final spinning speed of 2000 rpm and cured in oven at 80° C. The cured film was immersed in distilled water for 4 days to leach out the salt particulates and diblocks copolymer and leave a porous structure in PDMS film (see FIG. 7).

Figure 8:
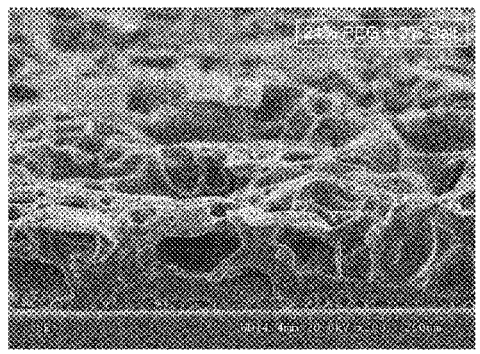
FIG. 8 shows the cross-section of a porous PDMS membrane: after leaching PEG and salt particles, porous PDMS structure was left behind.

Any water soluble polymer and particulates can be used using this method. A porous membrane can be loaded with different types of magnetic particles to achieve different magnetic behavior and can be bonded to the drug filled reservoirs by treating the surfaces with oxygen plasma. For example, Poly(ethylene Glycol): PEG, Mw=1450, was mixed with concentrations ranging from 20-50% w/w to PDMS and salt particles (1-5%. w/w to PDMS). PEG and salt was first mixed with PDMS prepolymer using the Thinky® conditioning mixer (AR-250) machine, followed by degassing for 40 min. The cross linker was added at a ratio of 5:1 for prepolymer to cross linker. The mix was spin-coated on a PAA sacrificial layer (described previously in example 2) and cured on a hot plate at 150° C. for 3 hours. The cured membrane was attached to the reservoir layer and placed in DI water to leach PEG and salt (see FIG. 8). For fabrication of porous magnetic membrane a process similar to fabrication of non-magnetic porous membrane was followed except that PEG was added to the magnetic composite that was previously prepared according to Example 1.

The continuity of porous PDMS was evaluated for various conditions as shown in FIG. 9.

Example 6

Construction of a Device Comprising a Magnetic Polymer Membrane a Reservoir Containing a Drug (Docetaxel) with Microsphere Containing Inlet/Outlet Pores A pumping membrane with a one-way micro fluid check valve to minimize background diffusion was made. The check valve was designed to be structurally thin and behave as a fluid diode under low pressure differences to enable pumping under low actuation pressures. The check valve has a channel height of 35 µm and uses 20 diameter µm polystyrene (PS) microspheres in the valve chamber. FIG. 10(a) shows the top view of the valve chamber. The valve chamber uses two sets of small square pillars with edges aligned 45° to the channel wall, to confine the PS microspheres. The square shaped PDMS pillars have a diagonal dimension of 40 µm width and are separated by 10 µm gaps. Larger circular pillars are used as structural supports to prevent channel collapse. The valve chamber has a reverse channel width WR in the reverse flow direction (to the left), and a forward channel width WF in the forward flow direction (to the right). A schematic of a reciprocating check valve pump is shown in FIG. 10(b). A magnetic membrane seals the pump chamber, and creates a stroke volume when deflected. FIGS. 10(c) and (d) show the top view of the check valve and pumping chamber, PS microspheres flow freely in the valve chamber moving with the flowing fluid. The flexible diaphragm is in its equilibrium position at the start of the pumping cycle. When an actuation force is applied, the pump chamber is compressed to its minimum volume and the resulting fluid flow forces microspheres away from the pump chamber illustrated in FIG. 10(c). The length of microsphere packing (porous media length) changes due to geometric effects in the check valve chamber as the diaphragm compresses and decompresses. The porous media lengths are represented as LR and LF respectively. With high resistance in the inlet check valve and low resistance in the outlet check valve a net flow out of the pump chamber through the outlet check valve is generated. When the actuation force is removed, the diaphragm returns to its equilibrium position, and causes microspheres to move towards the pump chamber shown in FIG. 10(d). With high resistance in the outlet check valve and low resistance in the inlet check valve there is a net flow into the pump chamber.

Figure 11:
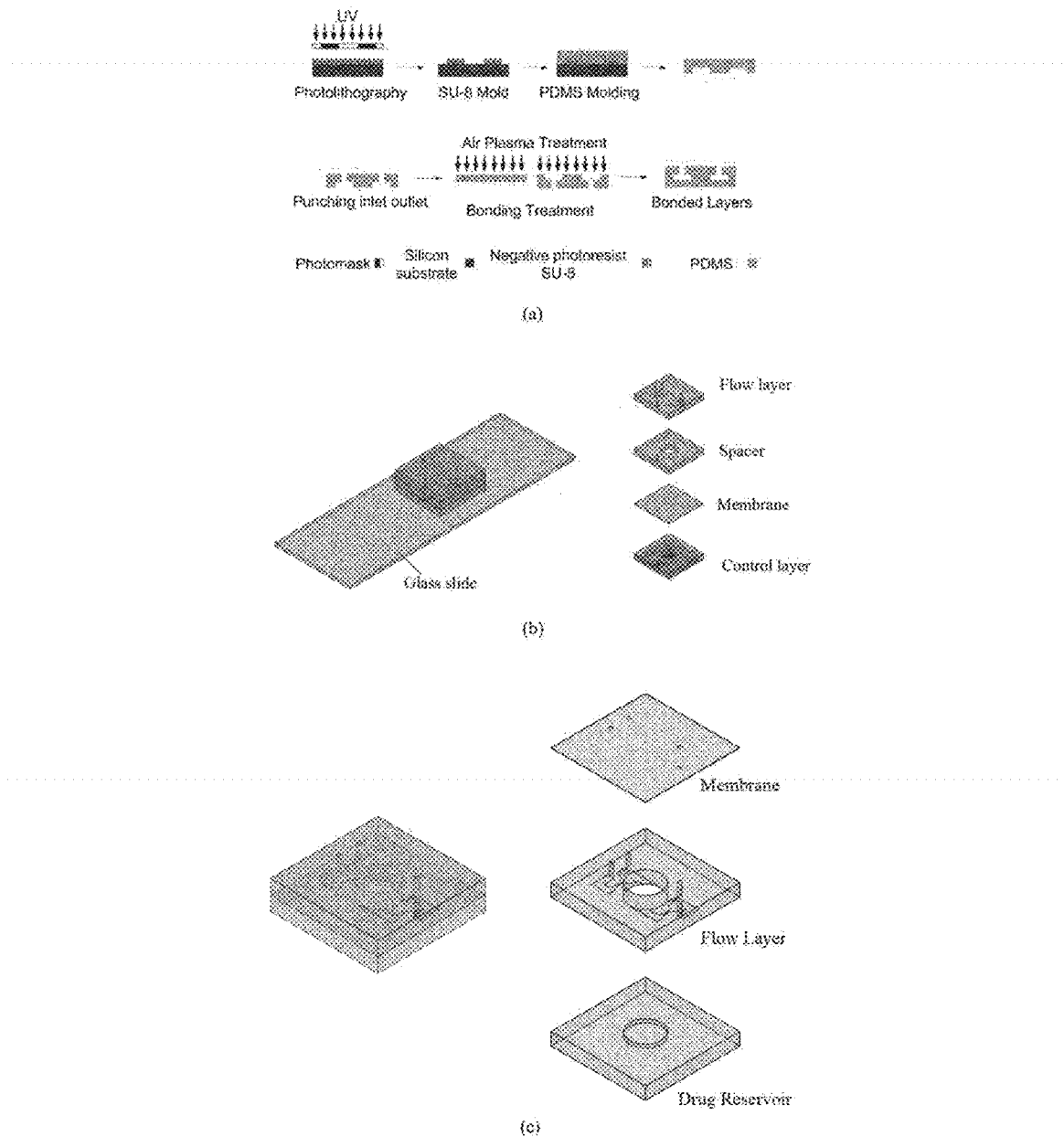
FIG. 11(a) shows soft lithography technique used in fabricating check valve and micropump.
FIG. 11(b) PDMS layers used to fabricate micropump in characterization experiments.
FIG. 11(c) PDMS layers of manually actuated micropump used in trial drug diffusion study.

Standard photolithography techniques were used to fabricate the negative molds used to replicate the flow layer and control layer of the check valve and micro pump. SU-8 molding of PDMS is used to form the valve and pumping layers. Detailed fabrication steps are illustrated in FIG. 11.

Figure 12:
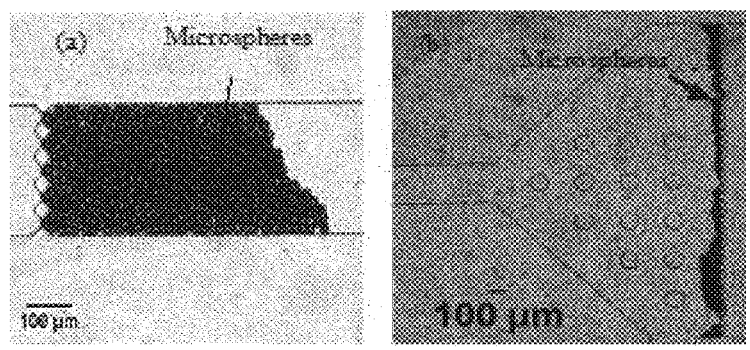
FIG. 12(a) shows microspheres collecting in reverse flow direction.
FIG. 12(b) shows microspheres collecting in forward flow direction.

FIG. 12 shows microspheres forming porous media at PDMS pillars in the reverse and forward flow directions. The diaphragm was actuated at each applied pressure three times and the volume flow through the inlet and outlet is shown in FIG. 13.(a). It shows that when the pump chamber compressed it generated flow through the outlet with low reverse flow through the inlet. On the other hand, when the pump chamber is decompressed a majority of fluid flows through the inlet and fluid is drawn back into the pump chamber from the surrounding environment. As expected, actuating the flexible diaphragm with increasing pressures led to increasing fluid volume displacement. FIG. 13(b) shows that the volume flow from the micro pump increased linearly as the input pressure increases. The micro pump displaced a volume of 0.25 µL with an applied pressure of 200 Pa and displaced a maximum volume of 1.26 µL at 1000 Pa. If placed in the conjunctival cul-de-sac the micro pump would draw fluid in the form of tears from the surrounding environment. Under normal conditions the estimated volume of tears in the conjunctival cul-de-sac is between 7 to 9 µL. Furthermore, the turnover rate of tear fluid is between 0.5 to 2.2 µL/min and the maximum fluid volume in the conjunctival cul-de-sac is 30 µL. Therefore, the micro pump performance falls within the conditions suitable for ocular drug delivery in the conjunctival cul-de-sac.

Diffusion comparison between a micro pump with microsphere in the check valve chamber versus a micro pump with no microspheres was conducted and the results are shown in FIG. 14 the average daily diffusion from the micro pump with no microspheres in the valve chamber was 56.32 ng. However, the average diffusion from the micro pump with microspheres in the valve chamber was 21.60 ng, representing a 62% reduction compared to the device with no microspheres. The error bars represent one standard deviation from the mean.

What is claimed is:

1. A drug delivery device comprising:
    a reservoir adapted to contain at least one deliverable; and
    a release mechanism sealingly engaged with the reservoir to selectively release the at least one deliverable upon application of an external stimulus, wherein the release mechanism is a diaphragm membrane further comprising a polymeric matrix which is substantially non-porous to the at least one deliverable in a first state, and porous to the at least one deliverable in a second state achieved in response to the external stimulus, wherein the polymeric matrix comprises a plurality of suspended magnetic particles, which upon application of a magnetic field causes displacement of the diaphragm to the second state.

2. The drug delivery device of claim 1, wherein the plurality of suspended magnetic particles are coated ferromagnetic particles, wherein the coating comprises one or more hydrophobic surfactants.

3. The drug delivery device of claim 2, wherein the one or more hydrophobic surfactants are selected from hydrophobic polymers, lipids, fatty acids, detergents, and mixtures thereof.

4. The drug delivery device of claim 1, wherein the diaphragm defines one or more pores that are substantially closed when in the first state and substantially open when in the second state.

5. The drug delivery device of claim 1, further comprising a deliverable of the at least one deliverable stored within the reservoir.

6. The drug delivery device of claim 5, wherein the deliverable comprises one or more active pharmaceutical ingredients.

7. The drug delivery device of claim 6, wherein the active pharmaceutical ingredient is selected from an antiangiogenic drug, an antiproliferative, an anti-inflammatory, an anticancer drug, an antiglaucoma, antiretinopathy drug, a drug that improves orthopedic outcome, or combinations thereof.

8. The drug delivery device of claim 1, wherein the device is sized and configured for implantation in one or more of under an eyelid, behind an eye, or intraocularly to treat ocular disorders.

9. The drug delivery device of claim 8, wherein the drug delivery device comprises a contact lens shaped device to release one or more drugs from the contact lens.

10. The drug delivery device of claim 1, sized and configured for implantation at or near a patient's body to be treated where the part of the body or disease to be treated is a pelvic fracture, bone fracture, urological, bone, cancer, arthritis, infections, ocular, neurological, endocrinological, vascular or inflammatory.

11. The drug delivery device of claim 1, wherein the diaphragm is made at least in part of the polymeric matrix, and wherein the polymeric matrix is made at least in part of the plurality of suspended magnetic particles.

12. A method for local release of a deliverable, the method comprising:
    positioning a drug delivery device at a site in need of receiving the deliverable, wherein the drug delivery device comprises:
        a reservoir adapted to contain at least one deliverable; and
        a release mechanism sealingly engaged with the reservoir to selectively release the at least one deliverable upon application of an external stimulus, wherein the release mechanism is a diaphragm membrane further comprising a polymeric matrix which is substantially non-porous to the at least one deliverable in a first state, and porous to the at least one deliverable in a second state achieved in response to the external stimulus, wherein the polymeric matrix comprises a plurality of suspended magnetic particles, which upon application of a magnetic field causes displacement of the diaphragm to the second state; and
    applying an external stimulus at or near the drug delivery device to release the deliverable.

13. The method of claim 12, wherein the external stimulus is applied at select intervals for a select duration to achieve a desired delivery profile.

14. The method of claim 12, wherein the external stimulus is a magnetic field.

15. The method of claim 12, wherein applying the external stimulus at or near the drug delivery device to release the deliverable causes the diaphragm membrane to move from a first position to a second position.

16. The method of claim 15, wherein movement of the diaphragm membrane from the first position to the second position causes a change of pressure within the reservoir which forces a substance through pores within the polymeric matrix.

17. The method of claim 15, further comprising removing the external stimulus to cause the diaphragm membrane to return to the first position from the second position.

18. A kit comprising:
    a drug delivery device comprising:
        a reservoir adapted to contain at least one deliverable; and
        a release mechanism sealingly engaged with the reservoir to selectively release the at least one deliverable upon application of an external stimulus, wherein the release mechanism is a diaphragm membrane further comprising a polymeric matrix which is substantially non-porous to the at least one deliverable in a first state, and porous to the at least one deliverable in a second state achieved in response to the external stimulus, wherein the polymeric matrix comprises a plurality of suspended magnetic particles, which upon application of a magnetic field causes displacement of the diaphragm to the second state; and
    a magnetic field generator.

19. The kit of claim 18, wherein the magnetic field generator is a magnet.

* * * * *